US008691165B2

(12) United States Patent
Duymelinck et al.

(10) Patent No.: US 8,691,165 B2
(45) Date of Patent: Apr. 8, 2014

(54) METHODS, REAGENTS, DEVICES AND INSTRUMENTATION FOR PREPARING IMPREGNATED TISSUE SAMPLES SUITABLE FOR HISTOPATHOLOGICAL AND MOLECULAR STUDIES

(75) Inventors: Carla Duymelinck, Kruibeke (BE); Mark Kockx, Edegem (BE)

(73) Assignee: Histogenex N.V., Edegem (BM)

(*) Notice: Subject to any disclaimer, the term of this patent is extended or adjusted under 35 U.S.C. 154(b) by 533 days.

(21) Appl. No.: 11/997,285

(22) PCT Filed: Jul. 31, 2006

(86) PCT No.: PCT/EP2006/007576
§ 371 (c)(1),
(2), (4) Date: Jan. 29, 2008

(87) PCT Pub. No.: WO2007/014741
PCT Pub. Date: Feb. 8, 2007

(65) Prior Publication Data
US 2008/0206807 A1     Aug. 28, 2008

(30) Foreign Application Priority Data
Jul. 29, 2005   (WO) ................. PCT/EP2005/008253

(51) Int. Cl.
*A61B 10/00*   (2006.01)
(52) U.S. Cl.
USPC ............... 422/536; 422/63; 422/50; 422/501; 422/502; 422/554; 436/180
(58) Field of Classification Search
USPC ............... 422/63–67, 50, 501–502, 536, 554; 220/560; 215/200; 436/180
See application file for complete search history.

(56) References Cited

U.S. PATENT DOCUMENTS 3,350,220 A * 10/1967 Isreeli .......................... 427/2.13
3,997,656 A  12/1976 Wertlake et al.
(Continued)

FOREIGN PATENT DOCUMENTS

DE   102 40 814   3/2004
EP   0 077 477   4/1983
(Continued)

OTHER PUBLICATIONS

International Search Report dated Mar. 16, 2007.

*Primary Examiner* — Jyoti Nagpaul
(74) *Attorney, Agent, or Firm* — Knobbe, Martens, Olson & Bear LLP

(57) ABSTRACT

A process for the production of paraffin sections of biological tissue, especially for molecular pathology studies is disclosed. In the process, the tissue sample is simultaneously fixed, dehydrated and cleared in a first step, subsequently dehydrated and cleared in a second step and infiltrated with an inert specimen matrix in a third step. The specimen can then be further embedded in a casting supporting matrix according to the standard procedures followed by any local pathology or research laboratory. A kit and a processing station for automating paraffin embedding of a tissue sample suitable for histopathological and molecular analysis is also described. A bio-indicator system is described for measuring the degree of crosslinking. A tissue sample holding means or a vial which includes a tissue sample holding means provided with a data logging device capable of registering and transmitting data regarding the sample and conditions where the sample was processed is also disclosed.

22 Claims, 27 Drawing Sheets

(56) References Cited

U.S. PATENT DOCUMENTS

| | | | |
|---|---|---|---|
| 4,141,312 A * | 2/1979 | Louder et al. | 118/702 |
| 4,483,270 A | 11/1984 | Toya et al. | |
| 4,857,300 A | 8/1989 | Maksem | |
| 4,935,875 A * | 6/1990 | Shah et al. | 702/22 |
| 4,960,224 A | 10/1990 | Boenisch | |
| 5,023,187 A | 6/1991 | Koebler et al. | |
| 5,089,288 A | 2/1992 | Berger | |
| 5,104,464 A | 4/1992 | Hasegawa | |
| 5,104,640 A | 4/1992 | Stokes | |
| 5,354,370 A | 10/1994 | Schmehl | |
| 5,424,040 A | 6/1995 | Bjornsson | |
| 5,482,591 A * | 1/1996 | Reo | 156/306.6 |
| 5,817,032 A * | 10/1998 | Williamson et al. | 600/562 |
| 5,869,689 A | 2/1999 | Zhang et al. | |
| 6,026,174 A | 2/2000 | Palcic et al. | |
| 6,095,734 A | 8/2000 | Postadan et al. | |
| 2001/0043884 A1 | 11/2001 | Essenfeld et al. | |
| 2001/0046426 A1 | 11/2001 | Lubera et al. | |
| 2002/0018733 A1 | 2/2002 | Kapplein et al. | |
| 2002/0030598 A1 | 3/2002 | Dombrowski et al. | |
| 2002/0071475 A1 | 6/2002 | Betzner et al. | |
| 2002/0100146 A1 | 8/2002 | Ko | |
| 2002/0131896 A1 | 9/2002 | Hunnell et al. | |
| 2002/0167187 A1 | 11/2002 | Murar | |
| 2002/0177183 A1 | 11/2002 | Giberson et al. | |
| 2004/0253662 A1 | 12/2004 | Heid et al. | |
| 2005/0145048 A1 | 7/2005 | Moir et al. | |
| 2008/0103114 A1 | 5/2008 | Zeligs | |
| 2008/0274496 A1 | 11/2008 | Duymelinck et al. | |

FOREIGN PATENT DOCUMENTS

| | | |
|---|---|---|
| EP | 1 130 377 | 9/2001 |
| EP | 1 186 787 | 3/2002 |
| EP | 1 455 174 | 9/2004 |
| GB | 2 379 739 | 3/2003 |
| WO | WO 99/09390 | 2/1999 |
| WO | WO 01/44783 | 6/2001 |
| WO | WO 01/44784 | 6/2001 |
| WO | WO 03/029845 | 4/2003 |
| WO | WO 03/031064 | 4/2003 |
| WO | WO 03/040697 | 5/2003 |

* cited by examiner

METHODS, REAGENTS, DEVICES AND INSTRUMENTATION FOR PREPARING IMPREGNATED TISSUE SAMPLES SUITABLE FOR HISTOPATHOLOGICAL AND MOLECULAR STUDIES

CROSS-REFERENCE TO RELATED APPLICATIONS

This application is the U.S. National Phase under 35 U.S.C. §371 of International Application PCT/EP2006/007576, filed Jul. 31, 2006, which claims priority to PCT/EP2005/008253, filed Jul. 29, 2005.

BACKGROUND OF THE INVENTION

Many researchers experience a trade-off between maintaining cell morphology and preserving gene expression information in the same tissue sample. Paraffin-embedded tissue samples generally show good morphology but gene expression data are severely compromised. Conversely, frozen tissue samples remain the gold standard for obtaining high quality gene expression information, but tissue morphology from frozen material is inferior compared to the morphology of paraffin-embedded tissue samples. Given the empirical foundation of microscopic analysis for current methods of tissue diagnosis and prognosis, the transfer of molecular methods into pathology practice has been greatly hampered. Indeed, the development of improved methods for tissue processing for transcript profiling of pathological samples are still necessary (Perlmutter M A, Best C J, Gillespie J W, Gathright Y, Gonzalez S, Velsaco A, Linehand W M, Emmert-Buck M R, Chuaqui R F: Comparison of snap freezing versus ethanol fixation for gene expression profiling of tissue specimens. J Mol Diagn 6(4):371-7, 2004). For gene expression analysis, the presence of intact and extractable nucleic acids from the test material is mandatory. Because the emerging role of transcript profiling studies in research and clinical work, a nucleic acid-friendly fixative with the morphological detail of formalin-fixed paraffin-embedded (FFPE) tissues should replace formalin as the primary (human) tissue fixative.

The cellular abundance of a particular RNA transcript is tightly regulated by the balance between its transcription and degradation rate. It is important for gene expression studies that the measured RNA population reflects the actual transcriptosome present at the time of tissue or cell collection as closely as possible. As RNA is rapidly degraded by ribonucleases, it is of paramount importance to reduce or halt endogenous enzyme activity as quickly as possible prior to or at the time of tissue or cell collection. One way of accomplishing this 'status quo' situation is by freezing techniques such as snap-freezing in liquid nitrogen. However, as known by those persons skilled in the art, the freezing process results in suboptimal microscopical detail of tissue architecture and cell morphology. Moreover transport of frozen tissues requires specialist shipment and is more costly and risky (chance of defrosting) than transporting paraffin-embedded material. For example, if gene expression studies are performed in a central reference laboratory, e.g. in clinical trials, frozen samples have to be properly prepared for courier shipment. Sometimes, international sample carriage is not possible.

Another problem in the art is the limited tissue biopsy availability. A single small-sized biopsy (e.g. needle biopsy) may not provide sufficient tissue for both classical histopathological analyses and molecular pathology assays. Consequently, it may be required to collect two tissue samples which causes additional distress and injury to the patient.

The extraction of high molecular weight DNA from paraffin-embedded tissue has been reported (e.g. Dubeau L, Chandler L A, Gralow J R, Nichols P W, Jones P A: Southern blot analysis of DNA extracted from formalin-fixed pathology specimens. *Cancer Res* 1986, 46:2964-2969; Greer C E, Peterson S L, Kiviat N B, Manos M M: PCR amplification from paraffin-embedded tissues. Effects of fixative and fixation time. *Am J Clin Pathol* 1991, 95:117-124; Inoue T, Nabeshima K, Kataoka H, Koono M: Feasibility of archival non-buffered formalin-fixed and paraffin-embedded tissues for PCR amplification: an analysis of resected gastric carcinoma. *Pathol Int* 1996, 46:997-1004; Ren Z P, Sällström J, Sundström C, Nister M, Olsson Y: Recovering DNA and optimizing PCR conditions from microdissected formalin-fixed and paraffin-embedded materials. *Pathobiology* 2000, 68:215-217). However, prolonged exposure of tissues to the fixative formaldehyde results in irreversible cross-linking of proteins and nucleic acids, causing the maximum PCR amplicon size to be limited (Finkelstein S D, Sayegh R, Christensen S, Swalsky P A: Genotypic classification of colorectal adenocardnoma. *Cancer* 1993, 71: 3827-3838). In addition extensive fixation in formaldehyde leads to nucleic acid scission, further diminishing the efficiency of PCR-based analysis and amplicon size. Although DNA survives fixation and embedding reasonably well, RNA content is seriously decreased due to the combination of the presence of RNase activity in virtually all tissues and the use of excessive heating during the infiltration and embedding procedures of the tissue processing. Indeed, it is more difficult to obtain high molecular weight RNA from (archival) paraffin-embedded material. Extraction of RNA with a maximal length of 600 base pairs has been described (Stanta G, Schneider C: RNA extracted from paraffin-embedded human tissues is amenable to analysis by PCR amplification. *Biotechniques* 1991, 11:304, 306, 308; Krafft A E, Duncan B W, Bijwaard K E, Taubenberger J K, Lichy J H: Optimization of the Isolation and Amplification of RNA From Formalin-fixed, Paraffin-embedded Tissue The Armed Forces Institute of Pathology Experience and Literature Review. *Mol Diagn* 1997, 2:217-230; Goldsworthy S M, Stockton P S, Trempus C S, Foley J F, Maronpot R R: Effects of fixation on RNA extraction and amplification from laser capture microdissected tissue. *Mol Carcinog* 1999, 25:86-91; Specht K, Richter T, Müller U, Walch A, Höfler M W: Quantitative gene expression analysis in microdissected archival tissue by real-time RT-PCR. *J Mol Med* 2000, 78:B27; Specht K, Richter T, Muller U, Walch A, Werner M, Hofler H: Quantitative gene expression analysis in microdissected archival formalin-fixed and paraffin-embedded tumor tissue. *Am J Pathol* 2001, 158:419-429; Paska C, Bogi K, Szilak L, Tokes A, Szabo E, Sziller I, Rigo J Jr, Sobel G, Szabo I, Kaposi-Novak P, Kiss A, Schaff Z: Effect of formaline, acetone, and RNAlater fixatives on tissue preservation and different size amplicons by real-time PCR from paraffin-embedded tissue. *Diagn Mol Pathol* 2004, 13:234-240).

However, such RNA fragment sizes severely limit the suitability of the RNA for certain molecular profiling applications such as the construction of full length cDNA libraries.

Even if the average RNA fragment size would be sufficiently large to allow paraffin-embedded tissues or cells to be used for RT-PCR, nucleic acid amplification procedures and microarray analyses, the reliability and reproducibility of quantitative gene expression studies are questionable in the presence of degraded and chemically modified RNA, especially since the different mRNA species from the mRNA pool are most likely not affected to the same degree/extent.

A number of fixative formulations have been described in the art. U.S. Pat. No. 6,319,683 is based on controlling the reactivity of the fixating components by quenching the excess formaldehyde with a formaldehyde reactive agent. U.S. Pat. No. 5,976,829 describes a fixative comprising aldehyde, alcohol and CDTA. WO 03/029783 describes the protection of the tissue specimen by impregnation with an osmotically buffered amino acid solution prior to fixation with an acetone-based fixative, which would obviate the need for a cross-linking agent. WO 00/06780 discloses a method for maintaining RNA integrity in biological materials by means of an RNA preservation medium. Although the patented medium does keep the RNA intact (Mutter G L, Zahrieh D, Liu C, Neuberg D, Finkelstein D, Baker H E, Warrington J A: Comparison of frozen and RNALater solid tissue storage methods for use in RNA expression arrays. *BMC Genomics* 2004, 5:88), in histological applications a variable outcome on tissue morphology and immunostaining has been observed (Florell S R, Coffin C M, Holden J A, Zimmermann J W, Gerwels J W, Summers B K, Jones D A, Leachman S A: Preservation of RNA for functional genomic studies: a multidisciplinary tumor bank protocol. *Mod Pathol* 2001, 14:116-128; Roos-van Groningen M C, Eikmans M, Baelde H J, de Heer H J, Bruijn J A: Improvement of extraction and processing of RNA from renal biopsies. *Kidney Int* 2004, 65:97-105).

U.S. Pat. No. 6,379,921 described a method using a procedure based on a zinc-containing aqueous fixative, an acetone-based clearing agent and molten resin. However, the resulting tissue blocks must be sectioned and processed differently from routine paraffin blocks which may complicate the work-flow in a routine pathology lab.

For future tissue conservation of pathology specimens, it would be desirable to satisfy both histological and molecular biological needs. An uncomplicated fixation and paraffin embedding method that results in tissue sections with the same morphological characteristics as formalin-fixed paraffin-embedded (FFPE) tissues, while preserving nucleic acid integrity would have an important impact on the feasibility and logistics of clinical trials. In addition, such method would greatly facilitate the introduction of gene expression analyses in routine pathology laboratories, especially if it requires no or only limited modification of standard routine downstream pathology protocols.

Tissue sample holders for holding tissue samples for histological examination are well known in the art. Such tissue sample holders or tissue sample cassettes can adopt variable forms. Most tend to adhere to a general design comprising an open-topped, box- or tray-like receptacle member and a cover member configured to matingly inter-engage with the receptacle member so as to close off the top opening in the latter, thereby defining an internal enclosure or chamber intended to accommodate a tissue sample. The inter-engagement between the said members is generally firm enough to prevent their separation during normal steps involved in sample processing, e.g., transfer between different containers, swirling or shaking movements, etc., yet allow intentional opening of the cassette by an operator in order to recover the tissue sample after completion of the processing. Moreover, in most cassettes at least the bottom plate of the receptacle member and/or the top plate of the cover member, and preferably both, are conducive to liquids so as to enable the exposure of the tissue sample enclosed in the cassette to liquid agents when the cassette is submerged in the latter. Typically, this may be achieved by provision of suitably sized and shaped perforations in the said plates. Exemplary, but non-limiting examples of tissue cassettes are disclosed, for example, in U.S. Pat. No. 3,674,396, U.S. Pat. No. 3,982,862, U.S. Pat. No. 4,220,252, U.S. Pat. No. 5,127,537, U.S. Pat. No. 5,821,115, U.S. Pat. No. 6,395,234 or WO 2006/060317.

During manipulation and processing of sample, a tissue sample is usually deposited into a solution comprising at least a fixation agent by the physician or his assistant already upon dissection of the tissue sample from a subject. Then the sample is usually sent to a histology laboratory for further manipulation. In view hereof, the total time for which the said sample is exposed to a fixative, and the conditions under which such exposure takes place, is only partly determined by the standardised procedures of a histology laboratory, but rather also greatly depends on how promptly the dissected tissue sample is delivered to the latter laboratory and at what conditions it has been kept in the meanwhile. Using prior art tissue cassettes it is very difficult to determine and monitor sample conditions between taking of the sample and further processing of the sample, e.g. in a laboratory.

Another object of the present invention is therefore to provide improved tissue sample holders for preparing tissue samples for morphological, immunohistochemical and/or molecular analysis. the invention also aims to provide improved tissue sample holders, which are capable of monitoring of logging of conditions, especially time and temperature, to which a sample is exposed in the course of its processing. Preferably, the invention aims to provide tissue sample holders capable of recording processing time of the tissue sample, as well as temperatures to which the sample was exposed during that time.

SUMMARY OF THE INVENTION

One embodiment of the present invention is a method for preparing a tissue sample, suitable for morphological and/or immunohistochemical analysis, and quantitative nucleic acid analysis molecular analysis comprising the steps of:
1) simultaneous fixation, dehydration and initial clearing of the sample using a fixation-dehydration-clearing, FDC, solution, that comprises a cross-linker and an excess of aliphatic or aromatic organic solvent,
2) dehydration and final clearing of the sample using a dehydrating-clearing solution, and
3) infiltrating the sample with an inert specimen matrix, ISM.

One embodiment of the present invention is a method as described above, wherein said FDC solution further comprises a hydrophobic solvent and a pH modifying substance.

One embodiment of the present invention is a method as described above, wherein said cross-linker comprises an aldehyde, preferably at a concentration between 0.2% and 10% (v/v).

One embodiment of the present invention is a method as described above, wherein said FDC solution comprises formaldehyde, methanol, diethylether and/or acetic acid.

One embodiment of the present invention is a method as described above, wherein said FDC solution comprises 0.2 to 10% of formaldehyde, 30 to 90% of methanol, 0 to 25% of diethylether and 0 to 10% of acetic acid.

One embodiment of the present invention is a method as described above, wherein the FDC solution consists of 10% of formaldehyde, 65% of methanol, 20% of diethylether and 5% of acetic acid.

One embodiment of the present invention is a method as described above, wherein said organic solvent is methanol.

One embodiment of the present invention is a method as described above, wherein said pH modifying substance is a weak acid.

One embodiment of the present invention is a method as described above, wherein said pH modifying substance is at a concentration between 0.1% and 10% (v/v).

One embodiment of the present invention is a method as described above, wherein said pH modifying substance is acetic acid.

One embodiment of the present invention is a method as described above, wherein said hydrophobic solvent is diethylether.

One embodiment of the present invention is a method as described above, wherein said hydrophobic solvent is at a concentration between 5% and 25% (v/v).

One embodiment of the present invention is a method as described above, wherein said dehydration-clearing solution comprises one or more of diethylether, dioxane or dimethoxypropane.

One embodiment of the present invention is a method as described above, wherein said ISM is low melting point paraffin.

One embodiment of the present invention is a method as described above, wherein said paraffin infiltrates the sample at a temperature between 45 and 56 deg C.

One embodiment of the present invention is a method as described above, wherein step 1) further comprising the use of a crosslinking indicator to indicate the degree of fixation.

Another embodiment of the present invention is a kit comprising:
  a) an FDC solution consisting of a cross-linker and an excess of aliphatic or aromatic organic solvent,
  b) a dehydrating-clearing solution,
  c) an inert specimen matrix, ISM, for infiltrating the tissue samples, each in separate containers for separate and/or sequential application to the sample.

Another embodiment of the present invention is a kit as described above, wherein said FDC solution has one or more of the features as defined above.

Another embodiment of the present invention is a kit as described above, wherein said dehydrating-clearing solution is as defined above.

Another embodiment of the present invention is a kit as described above, wherein said ISM is low-melting paraffin suitable for impregnating the tissue at a temperature between 45 and 56 deg C.

Another embodiment of the present invention is a kit as described above, further comprising a crosslinking indicator system to indicate the degree of fixation.

Another embodiment of the present invention is an instrument for automation of the method as defined above.

Another embodiment of the present invention is an instrument as defined above comprising one or more of sample receiving means, means for dispensing FDC solution, means for dispensing dehydration-clearing solution, means for dispensing ISM to the sample, means for agitation and means for draining waste solution.

Another embodiment of the present invention is a tissue sample obtainable by to the method as defined above.

Another embodiment of the present invention is a use of an FDC solution as defined above for the preparation of a sample suitable for morphological and/or immunohistochemical, and molecular analysis.

Another embodiment of the present invention is data obtainable by using a paraffin-embedded sample that has been produced according to the method of the present invention.

Another embodiment of the present invention is data as described above, which is one or more of micrograph 2D or 3D (virtual) images of sections, morphological analysis data, nucleic acid concentration and integrity data and data from downstream nucleic acid analyses.

Another embodiment of the present invention is a processing station for preparing a tissue sample suitable for morphological and/or immunohistochemical, and molecular analysis, comprising:
  means (81) to receive a vial (84) of solution for fixation,
  means (82) to receive a vial (85) of solution for clearing,
  means (83) to receive a vial (86) of ISM,
said processing station configured to bring the sample (87) into contact sequentially with the contents of each vial, wherein the means (83) to receive a vial (86) of ISM is disposed with a means for regulating the temperature of said ISM vial.

Another embodiment of the present invention is a processing station as described above, wherein said means (81) to receive a vial (84) of solution for performing fixation is disposed with a means for regulating the temperature of said fixation solution vial (84).

Another embodiment of the present invention is a processing station as described above, wherein at least one vial receiving means comprise fluid and optionally air access means.

Another embodiment of the present invention is a processing station as described above, wherein the respective vial receiving means are arranged as a vertical column.

Another embodiment of the present invention is a processing station as described above, wherein
  said means (81) to receive a vial (84) of fixation solution is positioned towards the centre of the column,
  said means (82) to receive a vial (85) of solution for clearing is positioned towards the top of the column, and
  said means (83) to receive a vial (86) of ISM is positioned towards the base of the column.

Another embodiment of the present invention is a processing station as described above, wherein said means (83) to receive a vial (86) of ISM comprises a vertically moving platform (121).

Another embodiment of the present invention is a processing station as described above, configured to process a sample held in the vial (84) of solution for fixation.

In yet another embodiment, the invention provides a processing station wherein the vials (84, 85, 86) are arranged in horizontal position. Preferably such processing station is further provided with means for determining the time for transferring said sample from one vial to another.

Another embodiment of the present invention is a vial (84) for use in the automated preparation of a tissue sample suitable for morphological and/or immunohistochemical, and molecular analysis, comprising a sample holding means (102) which is configured to immerse the sample in fluid held by the vial.

Another embodiment of the present invention is a vial (84) as described above, comprising at least one breakable seal towards the top of the vial, suitable for receiving or removing fluid therethrough.

Another embodiment of the present invention is a vial (84) as described above, comprising at least one breakable seal towards the top of the vial, suitable for applying positive or negative air pressure to the vial therethrough.

Another embodiment of the present invention is a vial (84) as described above, comprising at least one breakable seal towards the base of the vial, suitable for receiving fluid therethrough.

A further aspect of the present invention concerns additional improvements to apparatuses that can be employed for preparing tissue samples for morphological, immunohistochemical and/or molecular analysis.

In one embodiment the present invention relates to a tissue sample holding means which is configured to hold a tissue sample suitable for morphological and/or immunohistochemical, and molecular analysis, whereby the sample holding means is provided with a data logging device capable of registering and transmitting data regarding the sample and conditions wherein said sample is processed.

In a preferred embodiment said data logging device comprises means for monitoring time (t) during which said sample is processed. In a further preferred embodiment said data logging device comprises means for monitoring the temperature (T) of the sample in function of time (t). In another preferred embodiment, the data logging device comprises an on/off function adapted to activate/deactivate said data logging device. Preferably said on/off function is adapted to be activated manually, e.g. by opening/closing the sample holding means, or automatically, e.g. by means of suitable sensors or the like.

Another embodiment of the present invention is a tissue sample holding means, wherein said data logging device comprises a clock and/or timer.

Another embodiment of the present invention is a tissue sample holding means, wherein said data logging device comprises a thermometer.

Another embodiment of the present invention is a tissue sample holding means, wherein said data logging device further comprises a sensor capable of measuring electrical conductance.

Another embodiment of the present invention is a tissue sample holding means, wherein said data logging device comprises identification means capable of identifying said sample.

Another embodiment of the present invention is a tissue sample holding mean, wherein said data logging device comprises a memory storage component capable of storing said registered data.

Another embodiment of the present invention is a tissue sample holding means, wherein said data logging device is connectable to a reading device which is adapted to receive, read and process the data registered by said data logging device. Preferably said reading device is capable of analyzing the registered data and computing any necessary further processing conditions (e.g. time of processing) of the sample.

Another embodiment of the present invention is a tissue sample holding means, wherein said tissue sample holding means comprises a tissue sample cassette and whereby said data logging device is provided on said tissue sample cassette, preferably in a cavity (218) of said tissue sample cassette. In a preferred embodiment, the data logging device is embedded in a suitable matrix in a cavity of said tissue sample cassette.

In yet another aspect, the invention relates to a system comprising
  a tissue sample holding means, which is configured to hold a tissue sample suitable for morphological and/or immunohistochemical, and molecular analysis, whereby the sample holding means is provided with a data logging device capable of registering and transmitting data regarding the sample and conditions wherein said sample is processed, and
  a resealable lid connected to said tissue sample holding means by means of an elongated member.

Preferably the tissue sample holding means is as defined herein.

In another aspect, the invention relates to a vial configured to receive and retain liquids therein and a tissue sample holding means for securing a tissue sample therein, wherein said vial further comprises a data logging device capable of registering and transmitting data regarding the sample and conditions wherein said sample is processed. Preferably said data logging device is as defined herein. In another preferred embodiment, the vial comprises a resealable lid suitable for closing said vial whereby said lid is connected to said tissue sample holding means by means of an elongated member.

Another embodiment of the present invention is a vial wherein said data logging device is provided on said vial, on said lid, on said elongated member, or on said tissue sample holding means. Preferably said vial comprises at least one breakable seal towards the top of the vial, suitable for receiving or removing fluid therethrough. Said vial preferably also comprises at least one breakable seal towards the top of the vial, suitable for applying positive or negative air pressure to the vial therethrough. The vial may further comprise at least one breakable seal towards the base of the vial, suitable for receiving fluid therethrough.

Another embodiment of the present invention is a kit comprising a vial as defined above, where said vial contains FDC solution as defined above.

Another embodiment of the present invention is a as defined above, further comprising a vial of dehydrating-clearing solution as defined above.

Another embodiment of the present invention is a kit as defined above, further comprising a vial of ISM.

With the insight to better show the characteristics of the invention, some preferred embodiments and examples are described hereafter referring to the enclosed figures.

DETAILED DESCRIPTION OF THE PRESENT INVENTION

Figure 1:
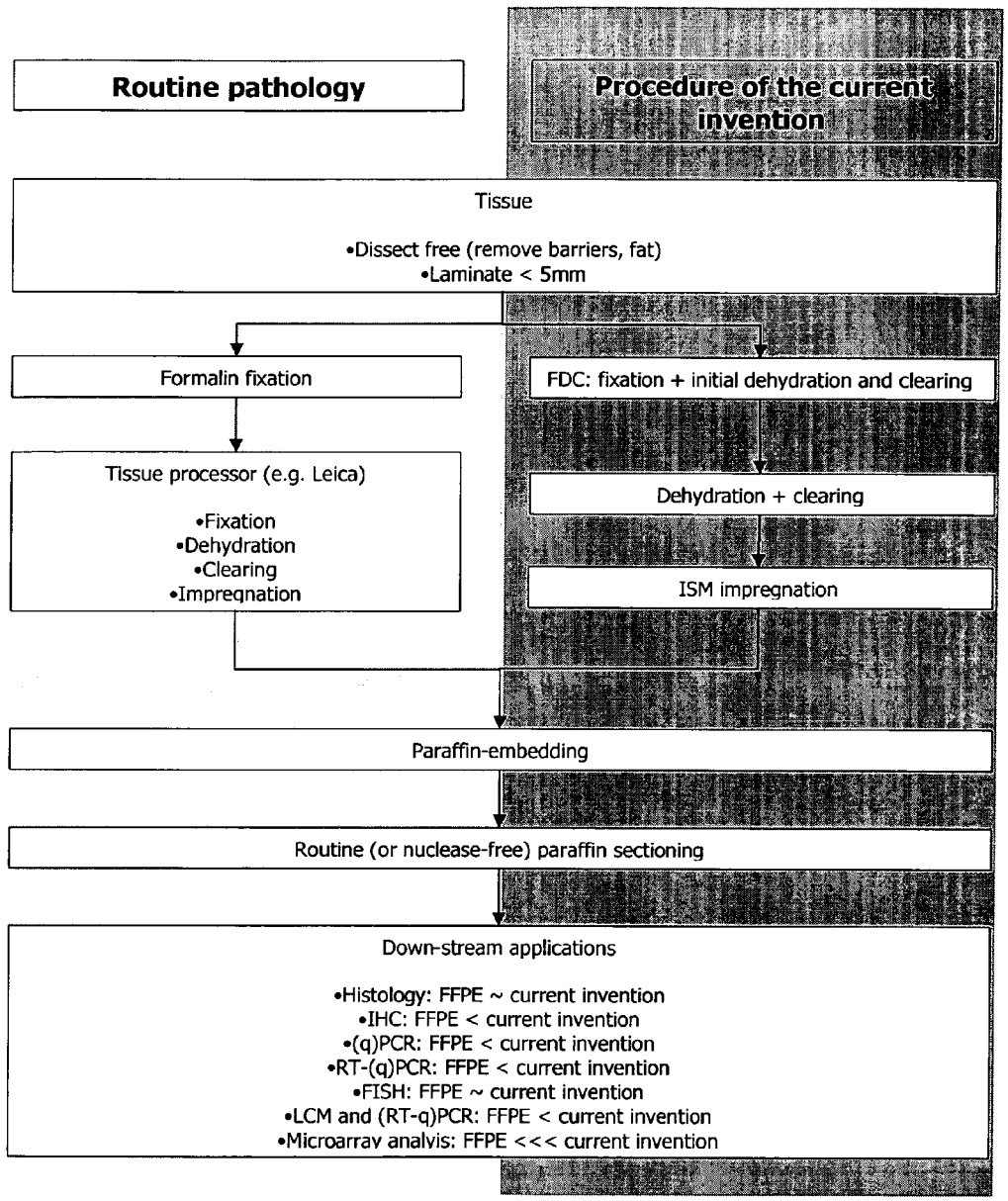
FIG. 1 is a flow chart showing an exemplary general manner of tissue processing as it is performed in a routine pathology laboratory. It further shows how the present invention can be uncoupled from and subsequently brought back into the routine pathology laboratory work-flow.

The present invention is concerned with a sample processing method for the production of sections that are suitable for morphological and/or immunohistochemical analyses, and for molecular analysis (e.g. nucleic acid analysis, quantitative nucleic analysis, qualitative nucleic acid analysis etc), by following certain consecutive processes:
1) simultaneous fixation, dehydration and initial clearing of the sample using a combined fixation-dehydration-clearing solution, called FDC solution hereafter,
2) combined dehydration and final clearing using a dehydration-clearing solution, and
3) impregnation of the sample with an inert specimen matrix (ISM).

Samples processed as described in the present invention can be subsequently paraffin embedded according to local procedures applied in any routine pathology or research laboratory. The resulting paraffin embedded tissue blocks can be sectioned at room temperature.

The present invention also relates to an instrument and processing station for automation of the 3-steps procedure. It also relates to a kit of reagents for implementing the sample processing method according to the invention.

The present invention further relates to an improved tissue sample holding means which is configured to hold a tissue sample and to be placed in a fluid-containing vial. The improved sample holding means is provided with a data logging device capable of registering and transmitting data regarding the sample and conditions wherein said sample is processed. The invention further relates to said data logging device and to a system and a vial comprising a tissue sample holding means and a data logging device.

The articles "a" and "an" are used in this document to refer to "one" or to "more than one", for example, "a sample" means "one sample or more than one sample".

Within the scope of the present invention, a sample refers to a biological specimen undergoing preservation. The sample may be either a cell, a part of a tissue, part of an organ, part of a tumour, or combination of such components. The sample may be human in origin, or derived from mouse, rabbit, human, goat, mouse, rat, cow, calf, camel, llama, monkey, donkey, guinea pig, pig, chicken or sheep, or any other vertebrate, invertebrate or plant.

We present an invention that allows a controlled sample fixation/dehydration/clearing and impregnation with an ISM that can be fully standardized by using a maximum of three components (FDC solution, dehydration-clearing solution and ISM). The additional strength of the present invention is that each sample is processed in fresh uncontaminated reagents which enables maximal control of the specimen processing steps and a decrease of cross-centre sample processing variation during the pre-analytical phase.

Method

Step 1: The combined fixation-dehydration-clearing (FDC) step of the present invention rapidly preserves the cellular morphology while retaining the immunohistological profile intact and keeping the chemical modification of the nucleic acids to a limit. In addition to fixation, it simultaneously dehydrates and partially clears the sample. According to the present invention, the sample is incubated in a fixation-dehydration-clearing (FDC) solution comprising of a cross-linker, an excess of organic solvent and an acid.

The cross-linker may be any known in the art. Preferably it comprises an aldehyde. Preferably it comprises a formaldehyde. Formaldehyde used in the present invention is saturated aqueous formaldehyde which is known as a 100% saturated, 37% w/w, 40% w/v or a 13.3M solution. The quantity of formaldehyde in the present invention is expressed as the quantity of formaldehyde and not of the saturated aqueous formaldehyde. The quantity of cross-linking aldehyde present in the FDC solution is less than or equal to 13, 12, 11, 10, 9, 8, 7, 6, 5, 4, 3, 2, 1, 0.5, 0.2% (v/v), or a quantity between any two of the aforementioned values. Preferably, the quantity of cross-linking aldehyde is between 0.2 to 10% (v/v). Most preferably the percentage (v/v) of formaldehyde solution is 10%.

The organic solvent can either be an aliphatic or aromatic solvent. Preferably, the organic solvent is a mono- or polyalcohol, or a mixture thereof in any given ratio. Most preferably, the organic solvent is methanol. The quantity of organic solvent present in the FDC solution is less than or equal to 95, 90, 85, 80, 75, 70, 65, 60, 55, 50, 45, 40, 35, 30, 25, 20, 15% (v/v), or a quantity between any two of the aforementioned values. Preferably, the quantity of organic solvent is between 30 and 90% (v/v). Most preferably the methanol percentage is 65% (v/v).

The FDC solution may further comprise an acid that counteracts the methano-induced shrinkage of the cellular tissue components. In addition, the pH decrease caused by the addition of an acid increases the reactivity of formaldehyde by the formation of a carbonyl ion that results in faster fixation through reacting with alkenes and N, S and O ions. The acid may be a weak acid. The weak acid is added until the pH of the FDC solution is less than or equal to pH 7.0, 6.5, 6.0, 5.5, 5.0, 4.5, 4.0, 3.5, 3.0, 2.5, 2.0 or a value between any two of the aforementioned values, and is between preferably 2.0 to 7.0. Most preferably, the pH of the FDC solution is between 3.0 and 6.0. Alternatively, the quantity of weak acid present in the FDC solution may be less than or equal to 15, 14, 13, 12, 11, 10, 9, 8, 7, 6, 5, 4, 3, 2, 1, 0.5, 0.2%, 0.1% (v/v) or a quantity between any two of the aforementioned values. The weak acid is preferably acetic acid. The quantity of acetic acid is preferably between 0.1% and 10% (v/v), and most preferably 5% (v/v).

The FDC solution may further comprise a hydrophobic solvent which is soluble in the fixative solution. This solvent increases infiltration and dehydrates the specimen, thus preparing the sample for the actual dehydration-clearing step. The hydrophobic solvent may be an ether. Preferably, it is diethylether. The quantity of solvent present in the FDC solution may be less than or equal to 1.0, 2.0, 3.0, 4.0, 5.0, 6.0, 7.0, 8.0, 9.0, 10.0, 12.0, 14.0, 16.0, 18.0, 20.0, 22.0, 24.0, 26.0, 28.0, 30.0% (v/v), or a value between any two of the aforementioned values. Preferably, the solvent percentage lies between 15.0 and 25.0% (v/v). Most preferably the solvent percentage is 20%.

The simultaneous fixation-dehydration-clearing step may be performed by incubating the sample, with or without agitation, for a period of time in the FDC solution.

A typical tissue specimen may be incubated for less than or approximately 3, 6, 9, 12, 14, 16, 18, 20, 22, 24, 26, 28, 30, 32, 34, 36, 40, 44, 48, 52, 55, 60, 65, 70, 75, 80 hours, or for a time between any two of the aforementioned values. Preferably the sample is incubated between 3 and 24 hours.

A typical tissue specimen may be incubated in a volume less than or equal to 10, 20, 30, 40, 50, 60, 70, 80, 90, 100 volume parts of FDC solution per volume part of specimen, or in a volume between any two of the aforementioned values. Preferably the specimen is incubated in between 10 and 50 volume parts of FDC solution per volume part specimen.

Simultaneous to the fixation, the FDC solution also performs the task of dehydrating the sample. In the prior art such procedure is performed after the fixation by consecutive incubations in dehydrating agents. According to the prior art, removal of fixative and water from the tissue and replacing them with dehydrating fluid may take at least three incubations after fixation, increasing the sample manipulation (time) and consequently increasing the risk of inducing more sample damage. The present invention reduces sample manipulation time and the need for additional reagents by using an FDC solution which simultaneously fixes, dehydrates and clears the sample. The sample can be transferred directed to the clearing-dehydration solution in the next step, without the need for a dedicated dehydration step.

Routine pathology labs traditionally use 4% neutral buffered formalin (NBF). NBF is theoretically suited for preserving cell morphology by cross-linking proteins and to a lesser extent, nucleic acids. In reality, NBF also suffers from a number of drawbacks. The rate of fixation by neutral formaldehyde is variable and slow. Furthermore, the cross-linking process results in extensive chemical modifications of the nucleic acids, which inhibit further downstream enzymatic processing of the extracted nucleic acids, e.g. in PCR-based amplification assays.

Crosslinking Indicator

Step 1 of the present invention may incorporate a system for indicating the degree of fixation in the sample caused by the cross-linker. The degree indicated by the system may be caused by any type of crosslinker known in the art, such as aldehydes or formaldehyde, and so can be applied to methods besides the method disclosed herein.

According to one aspect of the invention, the crosslinking indicator system comprises the use of at least one crosslinking indicator in which a directly or indirectly measurable property changes proportionally to the activity of the crosslinker or to the degree of crosslinking achieved over time. The measurable property can be any of the art, such as, for example, an observable colour change, a colour change upon further processing, a change in polarisation, change in spectroscopic property, a change in light transmission, a change in light scattering etc. It is an aspect of the invention that said crosslinking indicator is one that can be crosslinked, such as, for example, extracellular matrix components, or collagen.

Said crosslinking indicator may be immobilised on a solid support, such as, for example, nitrocellulose, magnetic beads or any suitable polymeric support. Such crosslinking indicator can be contacted with the crosslinking agent the same time as the sample.

Such a crosslinking indicator system allows the operator of the invention to measure, document and quality control the pre-analytical fixation of any tissue processing method involving any crosslinking agent known to the prior art. This also enables samples processed in different laboratories to be standardised and calibrated.

One embodiment of the present invention is a method of the present invention, wherein step 1 further comprises the step of simultaneously contacting FDC with a crosslinking indicator system. Thus, both sample and a crosslinking indicator system contact the FDC at essentially the same time.

The cross-linking indicator system can be integrated into any process where cross-linking occurs, and needs to be monitored. It may be incorporated into any vial containing crosslinking agent, or be added as a separate unit to a vial containing crosslinking agent, or incorporated into a tissue processing apparatus or technology known to the prior art. The crosslinking indicator system can be incorporated into any method developed to analyse/measure the crosslinker induced (bio)chemical or biological alterations.

Step 2. In this step of the method, the sample is incubated in a dehydration-clearing solution. The dehydration-clearing solution completes the dehydration and clearing of the sample. The dehydration-clearing solution comprises a solvent that is miscible with both water and with the ISM. A purpose of step 2 is to prepare the sample for transition from the hydrophilic fixative to the hydrophobic embedding medium. It facilitates infiltration of the sample with ISM, it removes FDC solution and, thus, diminishes the reactivity of residual formaldehyde with the sample nucleic adds at the elevated temperatures used for impregnation and embedding the sample with ISM. It also acts to remove lipids that may shield specific tissue targets and to permeate plasma membranes. According to one aspect of the invention, the dehydration-clearing solution comprises one or more of diethyl ether, dioxane (1,4 diethylene dioxide) or dimethoxypropane (DMP). According to another aspect of the invention, the clearing solution preferably comprises diethylether.

A typical sample may be incubated in the dehydrating-clearing solution with or without agitation for less than or approximately 1, 2, 3, 4, 5, 6, 8, 9, 10, 10, 12, 14, 16, 18, 20, 24, 28, 32, 36, 40, 44, or 48 hours, or for a time between any two of the aforementioned values. Preferably said sample is incubated between 1 and 24 hours in dehydrating-clearing solution.

A typical sample may be incubated in a volume less than or equal to 10, 20, 30, 40, 50, 60, 70, 80, 90, 100 volume parts of FDC solution per volume part of specimen, or in a volume between any two of the aforementioned values. Preferably the specimen is incubated in 10 to 50 volume parts of FDC solution per volume part specimen.

The sample may be transferred to the specimen infiltration matrix without any further treatment.

Step 3. In this step of the method, the sample is impregnated with an inert specimen matrix (ISM) that serves to support the specimen and give it sufficient rigidity to enable sections to be cut. The sample is impregnated by the ISM in the liquid form, which solidifies during the embedding. The ISM can be polyester wax, ester wax, carbowax polyethylene glycol, paraffin, a mixture of paraffin with plastic polymers, araldite, aromatic polyepoxide, diethylene glycol distearate, epon, glycol methacrylate, polyethylene glycol-glycol methacrylate, acrylate and polyester resins or Lowicryl. The ISM is preferably hydrophobic. The ISM may solidify at room or at higher or lower temperatures, may be cured by UV irradiation or set after addition of a catalyst. The infiltrating medium may be paraffin. Preferably it is a low-melting paraffin.

Where paraffin is used, it can be any type suitable for infiltrating and embedding samples. Generally, the paraffin is solid at or below room temperature, but melts when heated. According to one aspect of the invention, the ISM used for impregnation is liquid at a temperature less than or equal to 37, 40, 41, 42, 43, 44, 45, 46, 47, 48, 49, 50, 51, 52, 53, 54, 55, 56, 58, 60 to 65 deg C., or a value between any two of the aforementioned values. The ISM is preferably paraffin which melts between 37 and 65 deg C. According to another aspect of the invention, the sample is impregnated with liquid ISM at a temperature between 50 and 60 deg C., and preferably at a temperature higher than or equal to 55 deg C. Unlike methods of the art, in the current invention, a single incubation in the ISM is sufficient. Methods of the art use at least two treatments for prolonged periods and at increased temperatures, which could lead to further nucleic acid degradation and modification.

The temperature at which the sample is impregnated with the ISM can be more important than the embedding temperature, because of the longer duration of sample impregnation. Nucleic acid uncoiling is a temperature-dependent process; in their native states DNA and RNA do not react to any extent with aldehyde cross-linkers. However when samples are heated to about 45 deg C. in the case of RNA and 65 deg C. in the case of DNA, aldehydes may begin to react with the nucleic acids. After uncoiling of DNA and RNA the aldehyde molecules gain access to the reactive moieties of the nucleic acids. Therefore, the infiltration should be performed at between 52 and 58 deg C., for a well defined time interval such as 10, 20, 30, 40, 50, 60, 70, 80, 90, 100, 110, 120, 130, 140, 150, 160, 170, 180, 240 minutes, or for a period in the range between any two of the aforementioned times. Preferably infiltration proceeds for between 60 and 180 minutes.

The impregnation medium and embedding medium may be the same or may differ.

After the sample has been impregnated, it is usually embedded in a suitable substrate according to methods known in the art, such as paraffin. According to an aspect of the invention, paraffin embedding is performed at 40 to 65, 55 to 65, preferably at 60 deg C.

The current invention employs a complete sample fixation and processing system, which comprises three components (FDC solution, dehydration-clearing solution and ISM) that can be fully standardised. The described tissue processing results in tissue ready for standard paraffin-embedding that has good morphological detail and minimally modified nucleic acids. The additional strength of the proposed method is that each sample is separately processed in fresh and uncontaminated solutions which enables maximal control of the tissue processing steps and a decrease of sample processing induced cross-centre variation during the pre-analytical phase. In addition, the method uses less solution types in smaller volumes compared with the prior art, being both ecological and economical.

The combination of different solvents in the FDC solution enhances the tissue infiltration rate and controls the concentration of the monomeric cross-linking aldehyde. This not only optimally preserves the cellular and nuclear morphology and the immunohistochemical profile but also prevents pronounced RNA degradation and modification.

Therefore, the present invention is particularly useful in those applications where excellent tissue morphology and immunohistochemical profile should be combined with downstream applications requiring superior RNA quality such as molecular profiling studies on laser capture microdisseded tissue and cells. Furthermore, the expensive and risky storage and transport of frozen tissue specimens is avoided. Both morphological, immunohistochemical and molecular data can be obtained from a single tissue biopsy when the tissue supply is limited.

Kit

A kit according to the present invention allows a skilled artisan to perform one or more steps of the method disclosed herein, in an uncomplicated manner. The kit may allow a method of the present invention to be performed without the need to measure or determine the concentrations of reagents, so enabling a fast and reproducible treatment of one or more samples.

A kit according to the present invention comprises at least one of the components described above for performing a method of the invention on a sample. According to one embodiment, a kit may comprise one or more of an FDC solution as defined above for simultaneous fixation, dehydration and initial clearing of the sample,
a dehydration-clearing solution as defined above and
an ISM for infiltrating samples as defined above,
each in separate vials for sequential or stand-alone application to the sample.

The kit may also incorporate the crosslinking indicator system described above. The system may be integrated into the vial containing the FDC solution. In addition, the (bio) indicator system may also be a separate unit that can be added to the first vial of the kit.

The kit may be 'one use only', in which case a single kit is sufficient for the treatment of a single sample. Alternatively, the kit may comprise reagents for the treatment of several samples and may comprise multiple single-use containers. Preferably, the kit is configured in a way that no dilutions, weighing or measurements need to be performed by the user.

A container may be any sealed or resealable vessel suitable for carrying a quantity of reagent. Examples include, but are not limited to screw cap vials, push cap vials, break-seal-to-open vials or syringes.

All kits according to the invention may comprise the stated items or combinations of items and packaging materials therefore. Kits may also include instructions for use.

The kit according to the present invention may comprise as few as three containers, one each for the FDC solution, dehydrating-clearing solution and ISM. In contrast methods of the prior art require several washes with clearing solution, additional solutions for dehydration and two treatments with impregnation sample matrix. A small and straightforward kit is both more economical to manufacture, transport and store, and is easier to use compared with those of the art.

According to one aspect of the invention, a kit comprises a collection of three vials, as described below, respectively containing FDC, dehydration-clearing solution and ISM.

Instrument

Another aspect of the invention is an instrument for automation of the subsequent steps of the present invention. The instrument comprises means for receiving a sample, means for dispensing FDC solution, dehydrating-clearing solution and ISM to the sample, optionally means for agitation and means for draining waste solution. It may also comprise a programming means so the present method can be reproducibly performed in the case of, for example, standardisations or comparative studies. It may also be equipped with temperature control. It may also comprise a system for temperature and/or time registration.

Processing Station

In describing embodiments of a processing station and vials below, reference is made to the drawings in FIGS. 8 to 12. However, the drawings serve only to illustrate the invention, and are not intended in any way to limit the invention.

Figure 8:
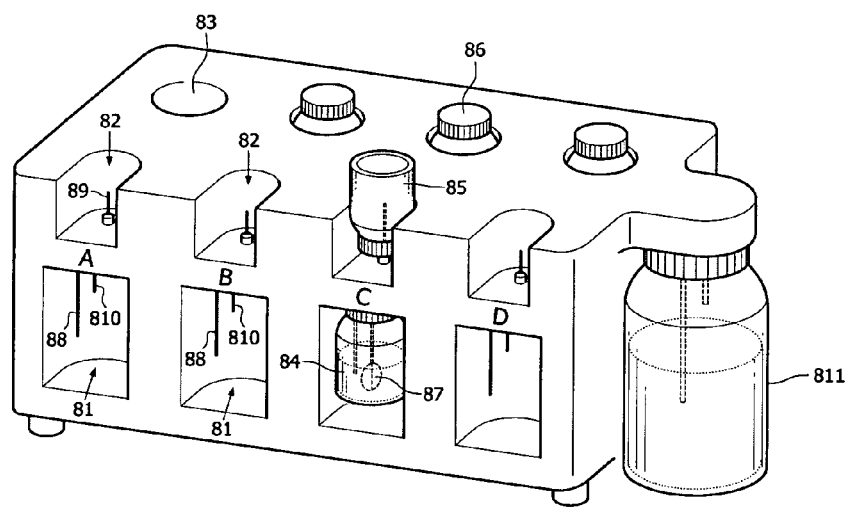
FIG. 8: A machine according to a preferred embodiment of the invention comprising four processing stations for the automated fixing, clearing and impregnation of four samples.

With reference to the drawing in FIG. 8, one aspect of the present invention is a processing station for preparing a paraffin embedded tissue sample suitable for histopathological and molecular analysis, comprising:

means 81 to receive a vial 84 of solution for performing fixation,
means 82 to receive a vial 85 of solution for clearing,
means 83 to receive a vial 86 of substance for inert specimen matrix (ISM), said processing station configured to bring the sample 87 into contact sequentially with the contents of each vial, wherein the means 83 to receive a vial 86 of ISM is disposed with a means for regulating the temperature of said ISM vial. By being able to heat the ISM vial, the ISM can be conveniently provided in a predispensed solid form for transport and storage, and melted and maintained in the molten state during processing. The automation of the device ensures consistent sample processing, critical for comparative studies, especially quantitative measurements. The vials can contain a pre-measured amount of reagent, so alleviating the burden of measuring reagent and reducing measuring errors.

FIG. 8 depicts a processing machine comprising four processing stations of the present invention (A, B, C, D) in a side-by-side configuration. The number of processing stations which can be incorporated into a single device can be one or more than one. Factors which can influence the number of stations in a processing machine include the space available, the specification of shared components (e.g. air and vacuum pumps) to serve a plurality of processing stations, cost etc.

According to a preferred aspect of the present invention a vial of solution for performing fixation contains FDC, a vial of solution for clearing contains dehydration-clearing solution, and a vial of ISM contains low melting point paraffin. Said three vial (step) method is described above.

Means to Receive a Vial

A means to receive a vial (vial receiving means, 81, 82, 83) may comprise at least one fluid access means (88, 89), so the contents of a vial can be accessed and transferring to a desired location. The fluid access means (88, 89) may be a hollow elongate member such as a tube, a needle, a nozzle etc. which preferably engages with a reciprocal feature on the vial, such as an opening, a septum or coupling.

The vial receiving means (81, 82, 83) may also comprise an air access means (810) to supply and extract air to a vial (84, 85, 86), so the contents of a vial can be emptied or filled by the application of pressurised air or a vacuum, or which can simply act as an air vent. The air access means (810) may be a hollow elongate member such as a tube, a needle, a nozzle etc. which preferably engages with a reciprocal feature on the vial, such as an opening, a septum or coupling.

The vial receiving means (81, 82, 83) may comprise a cavity with a base for holding the vial, the cavity walls at least partially enclosing the vial. The vial receiving means can be configured according to the action performed on the vial, according to the knowledge of skilled person. For example, where the vial receiving means (83) will hold a vial (86) of ISM in a molten state, the base and walls may be shaped to closely fit the outer shape of the vial. The wall may also be at least partially provided with heating and cooling means (e.g. heating elements, circulating cooling liquid, Peltier device).

In another example, where the contents of a vial are only to be emptied, the vial receiving means may be provided with just the fluid access means (89). Said fluid access means preferably engages with part of a breakable seal (91, 94, FIG. 9) present on the vial (85, 86)

In another example, a vial (84) may be used as the vessel in which the sample (87) is processed, as described below. In such case, during processing, the vial (84) is emptied, and later filled with a different solution; to facilitate emptying and refilling, the vial receiving means (81) may be provided with both the fluid access means (88) and air access means (810).

Said fluid and air access means preferably engage with corresponding breakable seals (92, 93, FIG. 9) present on the vial (84).

Where the vial (84) is used as the sample processing vessel, the base and walls of the vial receiving means (81) may be shaped to closely fit the outer shape of the vial and disposed with a means to regulate the temperature of the vial, so that the steps of fixation and clearing, for example, can be performed at a lower temperature than the steps of impregnation, and can be raised during impregnation.

Vials

A vial (84, 85, 86) for use in the processing station preferably contains sufficient solution for a processing step on a single sample. A vial may be made substantially of glass, polycarbonate, or any material of combination of materials compatible with the contents of the vial.

Figure 9:
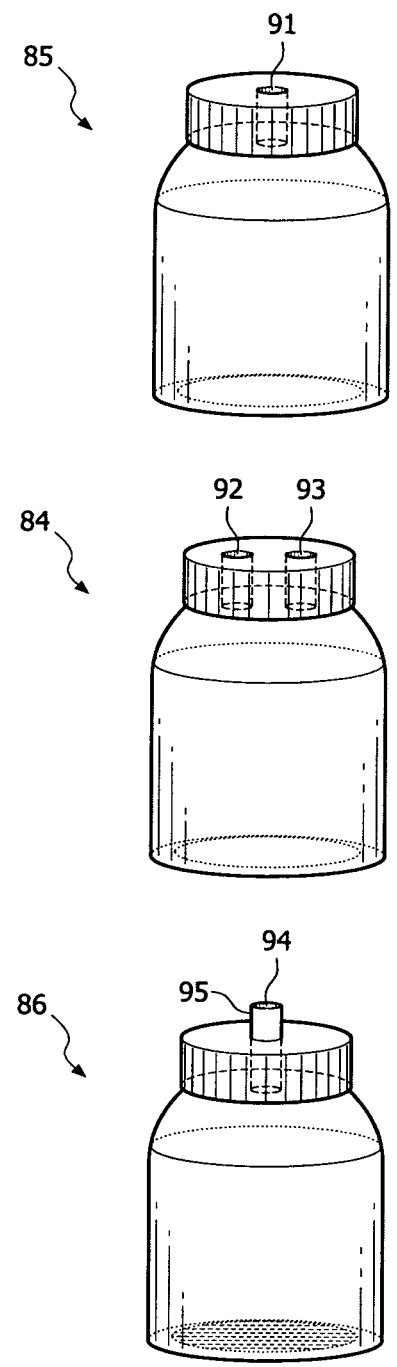
FIG. 9: Three vial according to a preferred embodiment of the invention suitable for use in the machine of FIG. 8 or FIG. 12.

With reference to FIG. 9, a vial for use in the processing station may be sealed with one or more breakable seals (91, 92, 93, 94) so that during storage and transport, the vial is sealed from the air. Prior to use, the seal may be broken by the operator, or a seal breaking means comprised in the vial receiving means. The breakable seal can be any suitable known in the art and can include a septum, a weakened joint which can be broken upon the application of force, a pull strip, a valve, a plug, a sealing bolt, a foil seal etc. A breakable seal can be resealable, or non-resealable. According to one aspect of the invention, the breakable seal is a foil seal breakable by the fluid access means and/or by the air access means. Preferably, a breakable seal is configured to engage with the fluid access means of the vial receiving means, and optionally another breakable seal may engage with the air access means of the vial receiving means. By engaging, a connection is made so that fluid and optionally air can enter and/or leave the vial. Preferably the connection allows air or fluid exchange under pressure or vacuum.

Fixation Vial

Figure 10A:
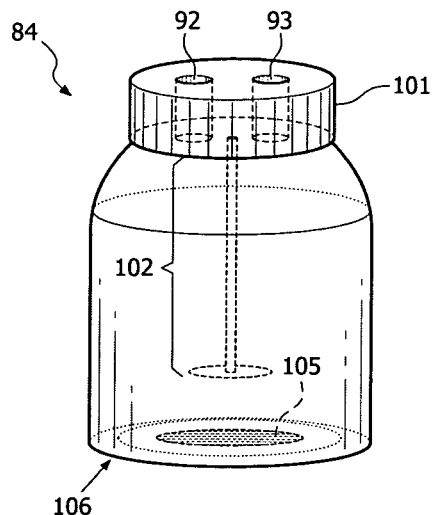
FIG. 10A: Vial according to a preferred embodiment of the invention for combined use as fixative carrier and sample processing vessel, suitable for use in the machine of FIG. 8 or FIG. 12.

With reference to FIG. 10A, another embodiment of the invention, is vial (84) suitable for holding fixation solution (e.g. FDC), comprising a means (102) to hold the sample. The sample holding means (102) is preferably configured to immerse the sample in the solution held by the vial. Such vial (84) can be the container in which the subsequent steps of processing are performed.

The sample holding means (102) can be incorporated into a resealable lid (e.g. screw cap) (101) of the fixation solution vial. Removing the lid (101) allows access to the sample holding means so the sample can be attached before and removed after processing.

Figure 10B:
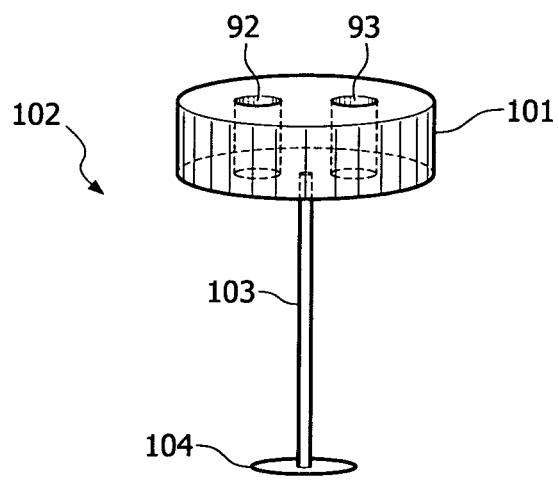
FIG. 10B: Detail of the lid and sample holding means of vial of FIG. 10A.
Figure 11:
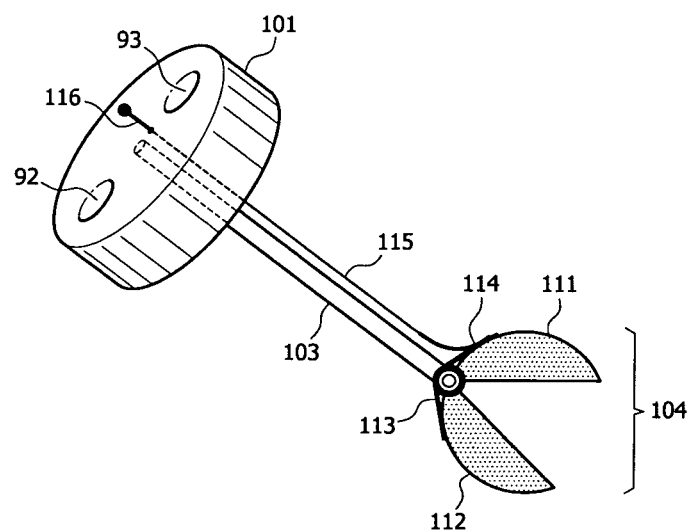
FIG. 11: Detail of according to a preferred embodiment of sample supporting means.

With reference to FIG. 10B, according to one aspect of the invention, the sample holding means comprises an elongate body (103) protruding from the resealable lid (101) of the fixation solution vial (84). The elongate body (103) ends in a means (104) to support the sample. The sample supporting means can be any suitable structure such as a gridded platform provided with a clip to hold the sample on the platform. With reference to FIG. 11, the sample supporting means can comprise a pair of jaws (111, 112) normally held shut by means of a stainless steel spring (113). The jaws can be opened by means of a wire (115) attached (114) to one jaw (111) which leads to an operating means (116) in the lid. Pulling on the wire (115) opens the jaw (111), allowing a sample to be placed between the jaws. Alternatively, the jaws may be configured so pushing on wire in the direction of the sample (115) opens the jaws, said configuration akin to that of a retracting sugar tong.

According to one aspect of the invention, the sample holding means (102) is disposed with a weight sensor for measuring the mass of the sample. The weight sensor can be built into the aforementioned means (104) to support the sample, for example. By measuring the mass of the sample, the times, temperatures and/or volumes of reagent can be adjusted to optimise the processing.

According to another aspect of the invention, the fixation vial receiving means (81) comprises a level sensor, which measures the level of the fixation fluid in the fixation vial. Thus, when a sample is introduced, the volume of fluid displaced by the sample can be determined, and accordingly, the volume of the sample. By measuring the mass of the volume, the times, temperatures and/or volumes of reagent can be adjusted to optimise the processing. In combination with knowledge of the mass of the sample, still more optimised conditions can be employed.

Another embodiment of the present invention is a fixation solution vial (84) as described herein, comprising a breakable seal (105, FIG. 10) for the entry of molten ISM.

According to one embodiment, the fixation vial (84) comprises at least one breakable seal towards the top of the vial, suitable for applying positive or negative air pressure therethrough. The fixation vial (84) may also comprise at least one breakable seal towards the top of the vial, suitable for receiving or removing fluid therethrough. The fixation vial (84) may also comprises at least one breakable seal towards the base of the vial, suitable for receiving fluid therethough.

In a preferred embodiment, the fixation solution vial is provided with a top lid (101) on which a sample holding means (102) and two breakable seals (92, 93) are provided for fluid and air access, and a breakable seal (105) on the base (106) of the vial for entry of the molten ISM. The seal on the base can be broken, for example, by a hollow tube inserted into the base. The hollow tube (95, FIG. 9) may protrude from the vial (86) carrying molten ISM, and allow molten ISM to flow therethrough. Preferably, the hollow tube (95) is located on the top of the ISM vial (86).

Vertically-Arranged Receiving Means

Figure 12:
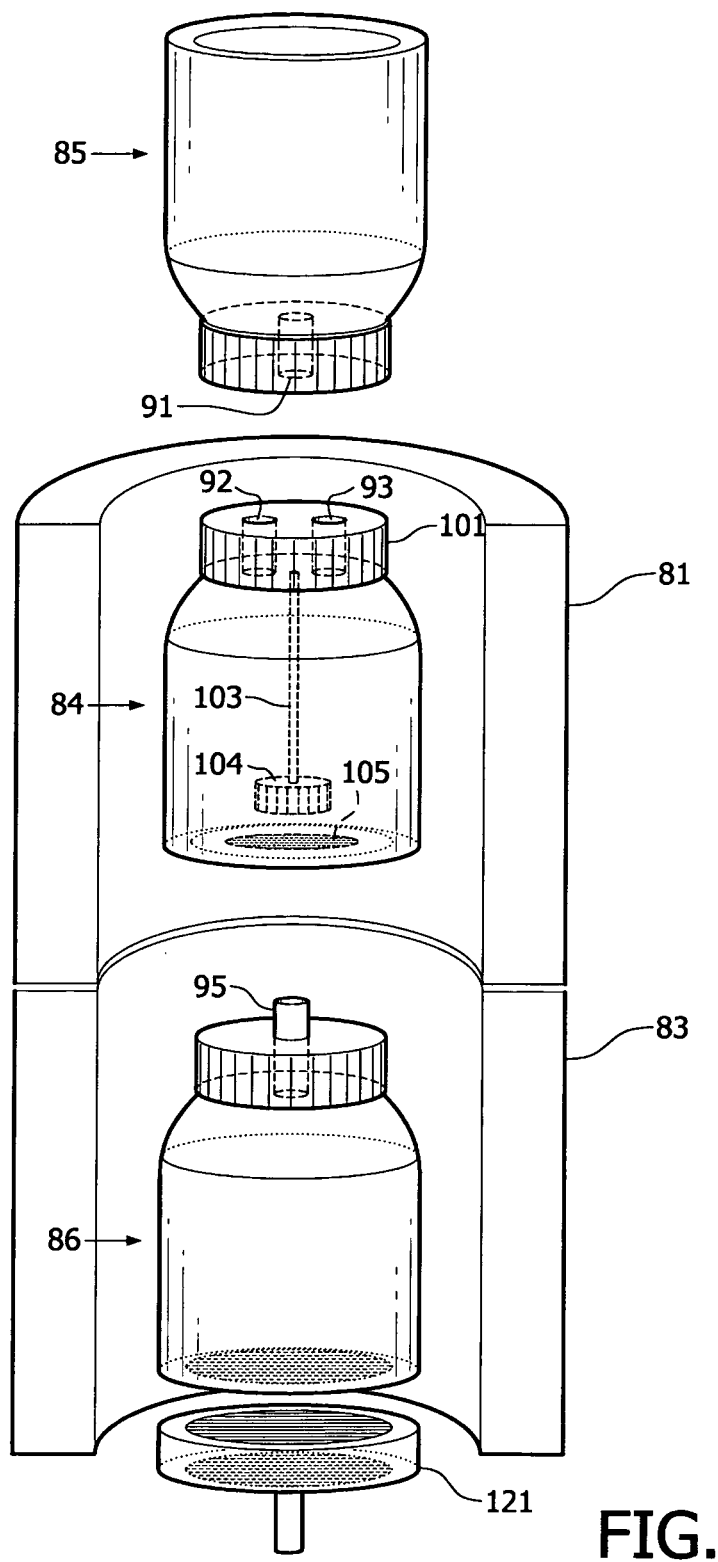
FIG. 12: Part of a preferred processing station where vials are vertically arranged.

According to one aspect of the invention, the respective vial receiving means are arranged essentially vertically along the same axis as shown, for example, in FIG. 12. Thus a column of essentially vertically arranged vial receiving means is formed. Preferably, the central axes of the vials are arranged essentially along a single axis. The fixation vial receiving means (81) can be placed in the centre of the column arrangement. Below may be placed the ISM vial receiving means (83) and above placed the clearing vial receiving means (not shown). The fixation vial receiving means (81) comprises fluid and air access means which can engage with the respective breakable seals (92, 93). The ISM vial receiving means (83) comprises a vertically moving platform (121) configured to move said vial (86) of ISM vertically. The platform which can move the vial (86) up and down to engage the hollow tube (95) on the top of the vial (described above) with a breakable seal (105) on the base of the fixation vial (84). Such platform can be operated hydraulically, by the use of levers, by rack-and-pinion assembly, or by any means known in the art. Both fixation vial receiving means (81) and ISM vial receiving means (83) comprise a cavity which walls are closely shaped to those of the vial and which contain means to heat or cool the sample. The clearing solution vial receiving means (not shown in FIG. 12) comprises a fluid access means which can engage with the vial.

The skilled person can readily implement a processing station as described above using, methods known in the art. The invention includes variations which the skilled person would implement in the course of carrying out the invention. The processing station can be configured with additional components to automatically perform the steps of fixation, clearing an impregnation. For example, a micro-processing means may co-ordinate the opening and closing of valves located between the access means. Such means and configurations are within the knowledge of the person skilled in the art implementing the invention.

Operation of the Processing Station

The following description refers to a mode of operation of a processing station. The skilled person can combine and adapt one of more the described steps according to the particular configuration chosen the processing station. During operation, the processing station is loaded with the vials containing fixation solution, clearing solution, and ISM. Upon loading, the seals in the vials can be broken by the respective vial receiving means where appropriate, and the fluid and optionally air access means of the processing station engage with the respective vials through the broken seals. The ISM vial receiving means is heated so as to melt the contents of the vial, while the fixation vial receiving means is preferably maintained at a lower temperature suitable for fixation and clearing. The sample is present in the fixation vial as described above. Once fixation has been completed as determined by time or by monitoring fixation using a crosslink indicator system, the fixation solution is removed by, for example, pumping air into the fixation vial and expelling the fixation solution out through the fluid access means into a waste jar. Clearing agent is then pumped into the fixation vial; this may be achieved by, for example, drawing air from the fixation vial via the air access means, and connecting the fluid access means of both the fixation and clearing receiving means. Thus clearing solution flows from the clearing solution vial to the fixation solution vial under vacuum. Once clearing is completed, the clearing solution is removed, for example, by pumping air into the fixation vial and expelling the fixation solution out through the fluid access means into a waste jar. The sample is then impregnated with molten ISM. This can be achieved as described above, for example, by drawing air from the fixation vial via the air access means, and connecting the fluid access means of both the impregnation and fixation vial receiving means. Where the processing station is arranged in a column fashion as described above, impregnation may proceed by raising the platform, and lifting the ISM vial. The tubular member pierces the breakable seal in the base of the fixation vial so forming a coupling. The movement may also open the breakable seal of the ISM vial. Once coupled, molten ISM can flow into the fixation vial by using, for example, vacuum pressure as described above. The temperature of the fixation receiving means can be raised during this step. After completion of impregnation, the molten ISM can be fed back into the ISM vial for cooling and disposal. Alternatively, it can be pumped into a waste jar.

A processing station according to the present invention is a simple and economic construction for processing a single sample, under precisely controlled conditions. Timings and volumes can be programmed, ensuring reproducibility across samples. The device uses vials containing predetermined concentrations and volumes of reagents which avoid the need for manual preparation and provides consistency between experiments and across different laboratories. In methods of the prior art, several samples are processed together in the same vessel, leading to mixing of cellular biomolecules such as, for example mRNA. The present device overcomes this problem by separately processing each sample. Because of the simplicity of construction, several processing station can be incorporated in a single device. The stations can share several components such as a processor, air and vacuum pump, waste lines etc, so even further reducing costs.

Tissue Sample Holding Means Provided with a Data Logging Device

In another aspect, the present invention relates to an improved tissue sample holding means.

In particular, the invention provides a tissue sample holder which is provided with a data logging device. Preferably said data logging device comprises following elements:

means for registering and transmitting data regarding conditions wherein said sample is processed. Preferably, the data logging device comprises means for monitoring the temperature (T) of the sample in function of time (t). Monitoring preferably takes place once the data logging has been activated.

means for providing identification data of the sample, e.g. data relating to the patient or physician, data relating to the tissue sample, means for measuring electrical conductance, and preferably also means for storing any data registered by the data logging device.

Tissue sample holders or cassettes are common receptacles used for storage and processing of tissue samples in histological applications. Providing a data logging device with the above-mentioned functions in a tissue sample holder advantageously allows to monitor and record the environmental conditions to which the tissue sample enclosed in the cassette is directly exposed. Moreover, by virtue of being provided with the same sample holder as the tissue sample, the data logging device remains in an unambiguous association with the particular tissue sample during the various treatment steps, thereby reducing the risk of errors in attributing the recorded data to a tissue sample exposed to the respective conditions.

The tissue sample holder and the above-enumerated elements and functions of the data logging device will now be further explained below.

Tissue Sample Holding Means

The term "tissue sample holding means" or "tissue sample holder" are used herein interchangeably and refer to any receptacle employed in the art, and in particular in the field of histology, for the storage and processing of tissue samples. In certain embodiments of the present invention, the terms tissue sample holding means is used as a synonym for a "tissue sample cassette".

Figure 21A:
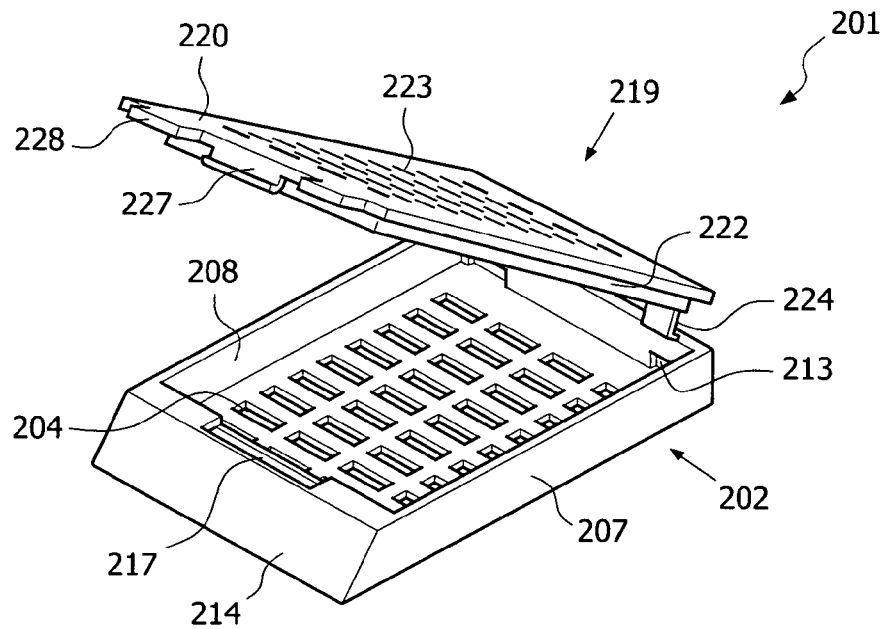
FIG. 21a is a perspective view of an embodiment of a tissue sample cassette according to the invention.
Figure 21B:
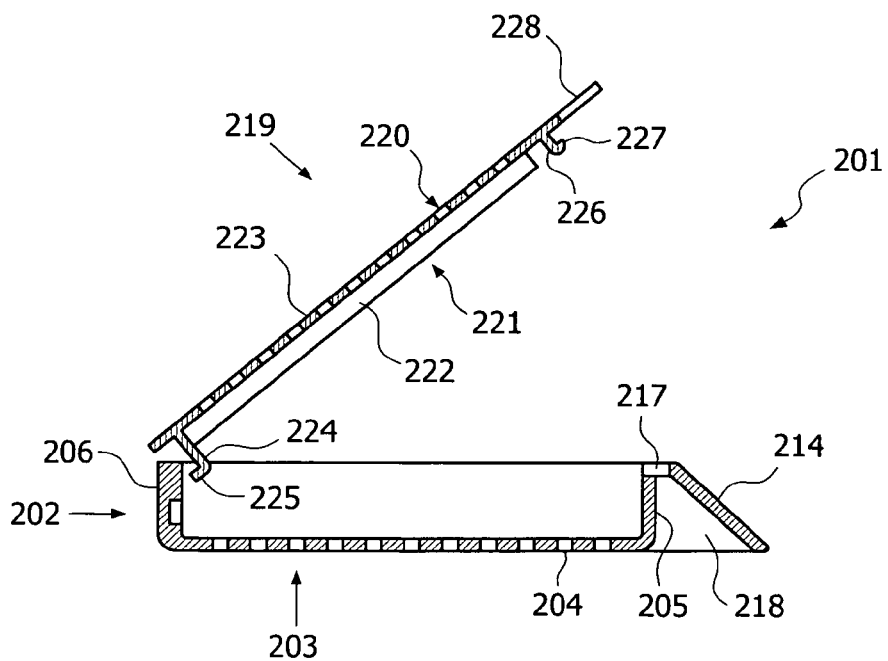
FIG. 21b is a lateral cross-sectional view of an embodiment of a tissue cassette according to the invention.

FIG. 21 a-b show an embodiment of a tissue cassette 201 as may be employed in the present invention in partly open configuration. The tissue processing cassette 201 comprises a receptacle or base member 202 and a cover 219 adapted to fit and cover said base member 202. The represented open-topped, box-like receptacle member 202 is formed in generally rectangular shape with a bottom wall 203 having a plurality of slot-like perforations 204 therein; opposing parallel first and second transverse endwalls 205 and 206 and opposing parallel third and fourth longitudinal sidewalls 207 and 208 extending upwardly from the bottom wall 203. One or more indentations 213 are formed in endwall 206. These indentations are conveniently rectangular in shape and form a first abutment means. Connected to and extending downwardly and outwardly from the upper edge portion 209 of endwall 206 is a slanted wall 214. The transverse endwall 205 is provided with a slot 217, which affords access to the transverse chamber 218 of generally triangular cross-section which is formed between the outer face of the transverse endwall 205 and the underside of the slanted wall 214.

The cover member 219 is formed as a flat plate having an upper surface 220 and a bottom surface 221. Cover member 219 preferably has a rectangular, box-like minor extension formed of walls 222 projecting outwardly from the bottom surface 221 of the plate. The external transverse and longitudinal dimensions of this minor extension are slightly less than the corresponding internal dimension of the open top of receptacle member 202. Flat plate of the cover member is formed with a plurality of slot-like perforations 223. Walls 222 extending from the cover plate 219 telescopically fit within the base member 202 when the cover member is mated against said base member. This relationship prevents any undesirable space from appearing between the cover and base members as a result of warping or distortion of the cover member during subsequent processing. This also prevents any undesirable loss of specimens during processing.

A first detent member 224 is formed on the cover member 219 in alignment with the indentation 213 on receptacle endwall 206 and may be generally of L-shaped cross-section. It comprises a horizontal tab 225 which has a transverse dimension slightly smaller than the corresponding dimension of indentation 213. The cover member 219 is provided with a second detent member 226 at the opposite end edge portion and in alignment with the base member slot 217, said detent member being formed of a vertically extending portion and an outwardly projecting horizontal tab portion 227. Tab 226 has a transverse dimension slightly smaller than the corresponding dimension of slot 217. A lifting tab 228 is formed on the outer end of the cover plate 219 and is coplanar therewith.

Base member 202 and cover member 219 may be conveniently moulded as a unitary combination structure, e.g., initially connected by a breakable hinge, from organoplastics, such as polyethylene, polypropylene, polystyrene, styrene-acrylonitrile copolymers, polycarbonate, formaldehyde homopolymers, copolymers of formaldehyde and trioxane, polyethylene terephthalate, polybutyleneterephthalate and the like.

In use, a tissue sample is placed within the receptacle member 202. The cover member 219 is then engaged to mate against the receptacle member 202. In so doing the tab 225 of the first detent member inter-engages indentation 213 of transverse endwall 206 and the tab 227 of the second detent member 226 is inserted through the transverse slot 217 and inter-engages the underside of the slanted wall 214. The inter-engagement of the above-described detent members and abutment members will prevent undesirable separation of the cover and base members during subsequent processing steps.

Data Logging Device

Time and Temperature

The invention provides a data logging device capable of registering and transmitting data conditions wherein said sample is processed. In a preferred embodiment, the data logging device comprises means for monitoring time. In another embodiment, the data logging device comprises means for monitoring temperature (T) of the sample in function of time (t). Preferably, the processing time of the tissue sample may be recorded, as may be the temperature to which the sample was exposed during that time.

As explained, preparation of tissue samples for histological examination may commonly involve several ensuing treatment steps, such as, e.g., fixation, which may be combined with initial dehydration and clearing according to one method aspect of the present invention; dehydration; clearing; impregnation with inert specimen matrix; and paraffin embedding. While most these steps are routinely carried out by a histology laboratory following standard conditions and protocols, the tissue sample is usually deposited into a solution comprising at least a fixation agent by the physician or his assistant already upon dissection of the tissue sample from a subject. Therefore, the total time for which the said sample is exposed to a fixative, and the conditions under which such exposure takes place, is only partly determined by the standardised procedures of a histology laboratory, but rather also greatly depends on how promptly the dissected tissue sample is delivered to the latter laboratory and at what conditions it has been kept in the meanwhile.

Yet, the extent of fixation may substantially affect the behaviour of a tissue sample in subsequent procedures. For example, incomplete fixation of the tissue may result in decreased morphological precision upon later microscopic examination. Conversely, over-fixation of the tissue sample may reduce the reactivity of antigens in ensuing immunohistochemical procedures, or may decrease the quality or quantity of nucleic acids, e.g., DNA or RNA, which may be detected in or isolated from such tissue sample.

Among the crucial parameters which tend to influence the extent of tissue fixation are, e.g., the time during which the tissue sample is exposed to a composition comprising a fixation agent and the temperature of the said composition. Longer times can achieve more extensive fixation than shorter times. Moreover, higher temperatures may advance fixation to a greater degree than lower temperatures. For example, higher temperatures can promote the diffusion of the fixative through the tissue sample, as well as aid the reactions which underlie the action of the fixation agent, such as cross-linking reactions.

It thus clearly follows that the way in which a tissue sample had been treated before it was delivered to a histology laboratory may affect its properties. Hence, for instance, a sample the physician had delivered within an hour following the actual dissection may behave distinctly from a sample delivered with a day or more delay. Likewise, a sample kept in the fridge may react differently than a sample stored on the shelf.

Faced with the above variability, the physicians are often asked to keep a logbook to record at least the time when each particular tissue sample was dissected or placed into a fixative. However, this solution is unsatisfactory. For example, it forces the physician or his assistant to divert their attention to recording written data, which may be experienced as a disturbance amidst dissections. Therefore, the physician may not comply or may prefer to postpone updating the logbook to a later time, as a consequence of which the so-recorded data may, albeit not intentionally, differ from reality. Further, such logbooks usually contain no information in regard of other conditions to which the sample has been exposed during fixation, most notably temperature.

Therefor, the present invention provides tissue sample holders, which are improved in that they are provided with a data logging device. Such device is capable of logging conditions, especially time and temperature, to which a sample is exposed in the course of its processing.

The present aspect will particularly help to control or reduce the above described variability in fixation conditions, thereby improving quality of the samples. For example, on the basis of the recorded information regarding the time elapsed since the isolation of a tissue sample or since the exposure of the sample to a solution comprising a fixative, and the temperature experienced by the sample during this time, a histology laboratory may decide whether, and if so how much, additional time is needed to satisfactorily complete the fixation of the sample. However, as will be appreciated by a skilled person, the data logging may also be continued during the further stages of sample processing beyond fixation, thereby offering a sounder overview of the processing history for tissue samples. Such sample processing history, including the data regarding fixation, may be advantageously consulted when, e.g., unexpected results are observed for a particular sample, in order to attribute such results to particular events of the sample processing history, or conversely to exclude such association.

In sum, the above arrangements provide for advantageous logging of temperature as a function of time for a tissue sample. Such data may help to normalise tissue sample processing, as they provide the information about the conditions to which the sample has been exposed in previous steps. In particularly useful application, these systems allow to determine the fate of the sample before this has entered a histology laboratory, and in particular the time and conditions of fixation and on basis thereof decide on the further processing of the sample.

In its simplest configuration, the invention relates to a data logging device comprising means for monitoring time (t) during which said sample is processed. For this, the invention provides in one embodiment a data logging device comprising a timer and/or clock. According to such embodiment, monitoring of the time may start from a first use of the data logging device on, e.g. when putting a sample in the tissue sample holder, or when placing the sample in a suitable fixation solution.

Said timer may be configured to measure a time interval which has elapsed from a discrete event that suitably "activated" the time keeping component. Advantageously, such time keeping component may be activated substantially concurrently with the deposition of a tissue sample into the respective tissue sample holder or with exposing the tissue sample holder to a first treatment solution, e.g., a solution comprising a fixative. In these instances, the time determined by the time keeping component as having elapsed since its activation will correspond to the time that the respective tissue sample is under processing.

In another embodiment, the data logging device comprises a clock i.e., to present the actual date and time applicable in a particular time zone, preferably the one in which the device is being used. This embodiment may provide the advantage that the date and time at which the tissue processing has been initiated can be recorded as a data point. In one embodiment, the data logging device may permanently measure the actual time, regardless of whether the tissue sample holder has been already put into use. In an alternative embodiment, the time keeping element may be "activated" while uploading the actual date and time thereto, where after it would continue performing as a clock.

In another embodiment, the data logging device comprises a thermometer. As indicated above, the present device allows taking a concurrent measurement of temperature and time. Hence, the device may record the temperature by means of its thermometer and associate the so-measured value with the time at which it has been obtained. In other words, the data logging device is able to measure temperature as a function of time. In view hereof, the data logging device may be configured, e.g., hardwired or instructed, to read a temperature at suitable time intervals, e.g., regular time intervals or irregular time intervals, depending on the exact protocol in which the tissue cassette is used. It is well within the ability of a skilled person to choose suitable time intervals for the temperature measurements. In non-limiting examples, the data logging device may perform a temperature measurement at intervals of about one second or shorter, about 1 minute, about 5 min, about 20 min, about 1 h, about 2 h or about 5 h.

Electrical Conductance

In another embodiment, the invention provides a data logging device capable of measuring electrical properties, such as the conductance, of the medium to which the data logging device is exposed. Such measurement may help to determine changes in the chemical compositions of the surrounding media, thereby registering the time at which the tissue sample holder has been transferred to a different solution. In one particularly useful embodiment, the measurement of a change in conductance may differentiate between the sample holder being exposed to gaseous phase such as air (e.g., before use) and being immersed in a liquid phase such as a solution (e.g., in the first processing solution, such as a fixation solution). The data logging device may be configured to automatically activate the measurement of temperature and, if not yet active, of time upon detecting such change, the latter being indicative of the fact that the cassette is now used for the processing of a sample.

Identification

In another embodiment, the invention provides a data logging device comprising identification means capable of identifying said sample. Such identification means are means that are able to register data related to the tissue sample. For example, relevant identification data may include a unique identification string of characters, data relating to the patient, such as, e.g., his or her name, surname, health insurance number, hospital reference, etc., or data relating to the tissue sample, e.g., type of tissue biopsied, type of biopsy, instructions of tests to be performed thereon, performing physician, etc.

Memory Storage Component

In another preferred embodiment, the present data logging device comprises a memory storage component capable of storing data registered by the data logging device. Such registered data may comprise, but is not limited to data regarding sample processing conditions, e.g. temperature in function of the time, sample identity (see above), etc. A skilled person will understand that, depending on the capacity of the memory storage component various other data may be stored thereon. The registered data is herein also referred to as to "data points".

The data storage capacity may be provided for by an external component, i.e., a component not comprised within the tissue sample holder. In such case, the data logging device may be configured to transmit the acquired data points, automatically or on request, via a suitable wireless or wired interface to the external memory storage component. The latter may typically form a part of a computing device. In an embodiment, the data points are not stored by directly transmitted—automatically or on request, via a suitable wireless or wired interface to the external memory storage component.

The data storage capacity may also be provided for by an internal component i.e., a component comprised within or on the tissue sample holder. In a preferred embodiment, such component may be integrally comprised in the data logging device. Alternatively, it may be provided separately on the sample holder and suitably interfaced with the data logging device.

Advantageously, the tissue sample holder in such embodiment would represent a stand-alone arrangement capable of recording and storing data points, e.g. regarding the temperature, to which it, and thus also the sample contained there within, have been exposed and at what times. Hence, the data relating to the sample would remain in direct association with the holder containing the sample, and could be readily read therefrom, thereby reducing the chances of erroneous attribution of data to wrong samples. An added benefit of a memory storage component included on a tissue sample holder, e.g., as an integral part of the data logging device, is that further identification data related to the sample may be uploaded to the memory storage component, thereby physically associating the said data with the tissue sample being processed in the holder.

Position of the Data Logging Device on the Tissue Sample Holder

In one embodiment, the data logging device may be provided on the tissue sample holder. For example, the tissue sample holding means may comprise a tissue sample cassette and the data logging device can be provided on said tissue sample cassette, as illustrated on FIG. 22 a-b. However, it will be clear, as further explained below, that the data logging device may also be provided on other parts of a tissue sample holder or on other elements (e.g. lid, vial) associated with such tissue sample holder.

In one embodiment, the data logging device is provided on a tissue sample cassette. The data logging device may be attached to essentially any portion of the cassette. However, in advantageous embodiments, such attachment may use void spaces present in this type of cassettes. In one example, the data logging device may be attached to portions of the cassette that define the chamber for receiving the tissue sample. Understandably, in this case the size of the data logging device will need to be such as not to considerably limit the dimensions of tissue samples that this chamber can accommodate. FIG. 22 a-b represents for instance a data logging device 230 that has been placed in the void space 218 delimited by the inner surface of the slanted wall 214 of the receptacle member 202. Most cassettes in common use include such frontal slanted wall 214, which facilitates marking and handling of the cassettes. Accordingly, most such cassettes may also include the above void space 218 which may thus be used to accommodate the data logging device. When the data logging device is deposited within such void spaces of tissue cassette, the overall profile of the cassette may advantageously remain unaltered, and the cassette may continue to be easily stackable or storable in containers, e.g., racks available for the said cassettes.

It may be preferred that the data logging device is attached to the receptacle member 202 rather than to the cover member 219. In particular, it is a common practice in histology to use the receptacle member 202 of a tissue processing cassette to provide a support for moulding a paraffin block containing the tissue sample having been processed in the said cassette. Therefore, if the data logging device is attached to the receptacle member 202, the association of the data logging device and therein recorded data with the sample may be continued during the lifetime of the respective tissue block, thereby further reducing the risk of sample swapping.

Figure 22A:
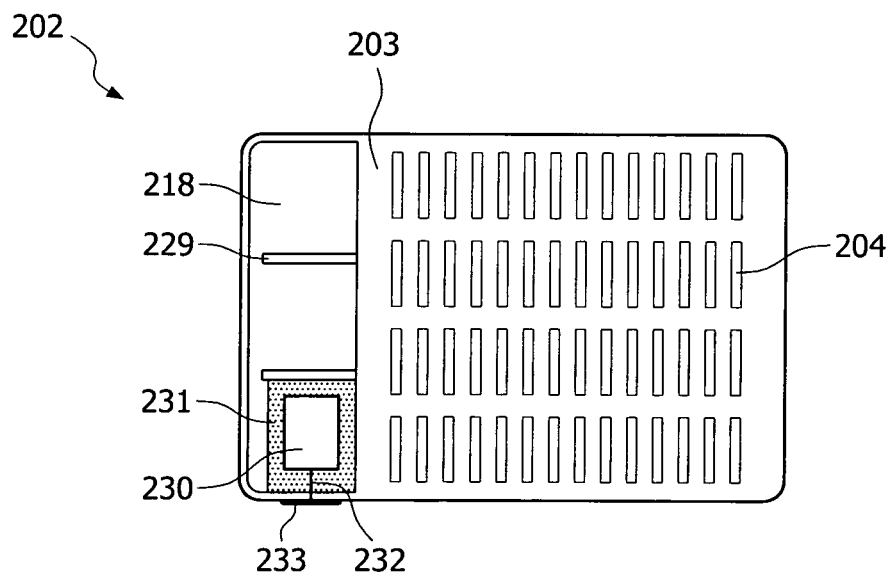
FIG. 22a represents a view of the underside of a tissue cassette according to the invention.
Figure 22B:
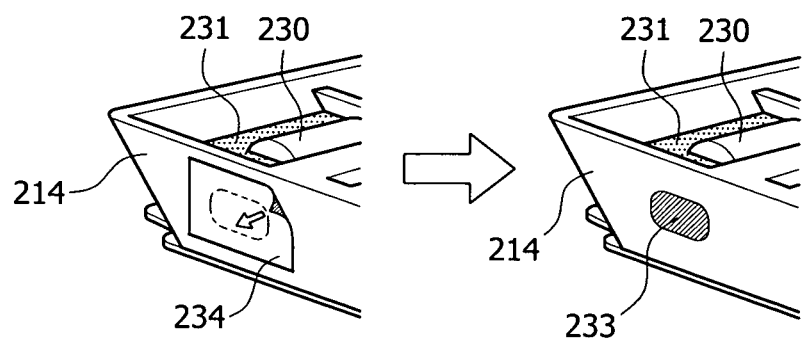
FIG. 22b represents perspective views of the data logging device embedded in a cavity at the underside of a tissue cassette.

The data logging device may be stably attached with the cassette by any means available in the art. In a preferred embodiment, the data logging means is embedded in the tissue sample cassette and provided with a suitable coating. For example, the data logging device and the cassette may be attached using an adhesive, by thermo-bonding, ultrasound bonding, or by means of embedding of the data logging device into a matrix, such as a suitable organoplastics matrix. FIG. 22a-b illustrates that the void space 218 under the under the slanted wall 214 is divided into several compartments by septa 229. In the illustrated embodiment, one of the compartments contains a data logging device 230 embedded in a suitable matrix material 231. In preferred embodiments, the matrix material 231 enclosing the data logging device 230 may not only facilitate the attachment of the latter to the cassette, but may also isolate and protect the data logging device from the action of the solutions to which the cassette may be exposed. Suitable embedding materials may include, e.g., epoxy polymers.

As thus follows from the above, the provision of the data logging device on the tissue processing cassette achieves that the data logging device is exposed to substantially the same physical conditions as the tissue sample within the cassette. In particular, being an integral part of the cassette, the data logging device can be submerged together with the cassette into the different reagent solutions used in the processing of the tissue sample, thereby directly measuring the parameters, esp. temperature, of the medium to which the sample is also exposed.

Secondly, and also advantageously, the provision on the cassette of the data logging device, especially in conjunction with a memory storage component configured to store the measured data points, esp. temperature vs. time, and possibly to store other data relevant to the identity or properties of the processed sample, provides for a close association between the processed tissue sample and the data relating thereto, during the whole or a substantial portion of the processing of the sample.

Data Transmission

In yet another embodiment, the invention relates to a data logging device which is connectable to a reading device. Said reading device is capable of reading and processing said registered data. The term "reading device" and "electronic device" are used herein interchangeably.

The data logging device may communicate with external electronic devices, such as computing devices or memory storage devices wirelessly or via a suitable wired interface. In FIG. 22a, the data logging device 230 is shown to contain a wired connection 232 lead ending in an interface 233, which can be contacted with a suitable read/write device in order to download data logged by the data logging device into the external device, or conversely, to upload instructions or data to the data logging device 230 or its memory storage component (e.g., instructions to initiate data measurement, or data relating to the sample stored in the cassette).

While the interface 233 may provided essentially anywhere on the cassette, it may be particularly feasible to provide it on one or more of the easily accessible surfaces of the cassette, and particularly of its base member 202. For example, in the illustrated embodiment (FIG. 22b), the interface 233 is provided on outer surface of the slanted wall 214, although its positioning on, e.g., the outer surface of a longitudinal sidewall of the base member may also be foreseen. As shown in FIG. 22b, the said interface 233 may be advantageously protected by a suitable tape 234, e.g., before it is used or during exposure of the cassette to the various treatments. This tape 234 may be reversibly removed to enable reading/writing of the data through this interface, and may be re-applied to further protect the interface.

Figure 23A:
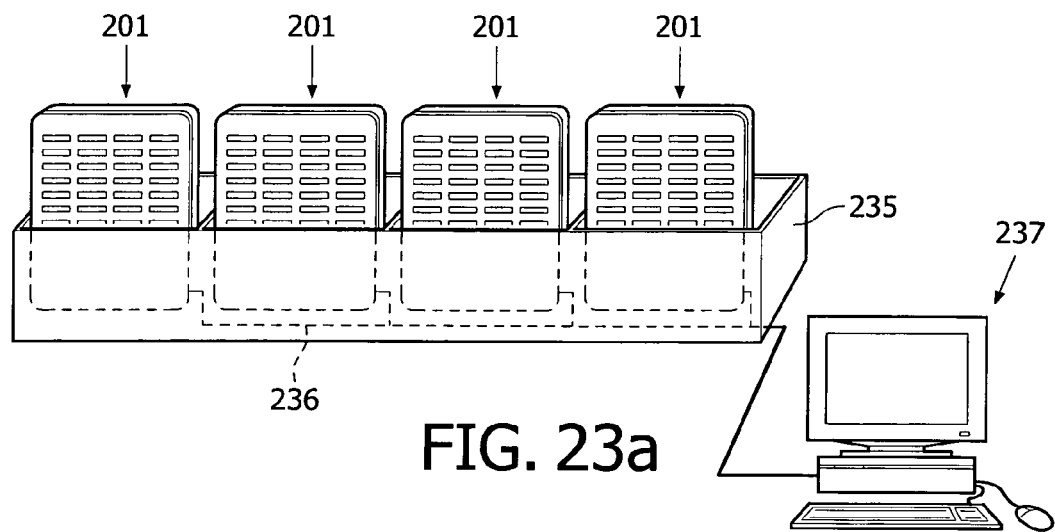
FIG. 23a-b illustrate storage racks for embodiments of tissue cassettes according to the invention.
Figure 23B:
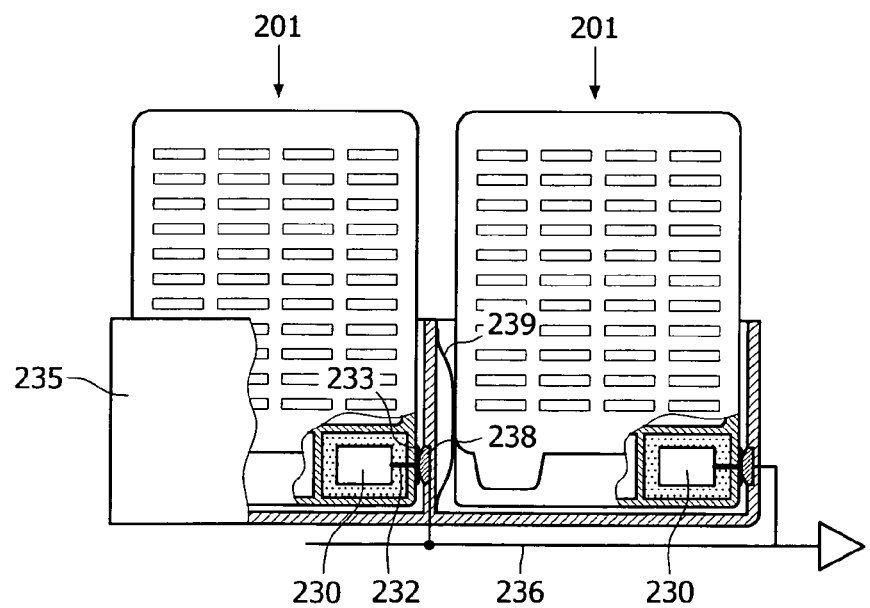

Further, as shown in FIGS. 23a-b, the cassette 201 may be stored, e.g., after having been processed, in a rack 235 which comprises communication means capable of connecting the data logging device 230 of the cassette 201 via the interface 233 to a read/write device 237, such as a computing or memory storage device. For example, one groove of the individual slots of the rack 235 in which the cassettes 201 are deposited may comprise an integrated interface 238 configured to co-operatively contact and communicate with the interface 233 of the cassette and relay data through a system of wired connections 236 to the associated read/write device 237. The close interconnection between the interfaces 233 and 238 may be facilitated by the tensioning means 239 provided in, e.g., the opposite groove of the slots of the rack.

Activation of the Data Logging Device

According to the present invention, the data logging device is capable of registering and transmitting data regarding the sample and conditions wherein said sample is processed once activated, for instance from the moment on that the sample is placed in the holding means or from the moment on that the sample holding means is placed in the liquid-containing vial. The data logging device is capable of being activated manually or automatically.

For example, when using the tissue cassette 201 according to the above embodiments, a physician performing a biopsy would depart from an empty cassette provided with a data logging device 230, optionally with tape 234 in place. He would deposit the biopsied issue sample in the cassette and would subsequently lock the cassette. Afterwards, the data logging device 230 would need to be activated by sending a suitable instruction thereto, e.g., either wirelessly or using the interface 233 from which the tape 234 would be removed for this purpose, such that the time-dependent measurement of temperature by the device 230 would be initiated. At this stage, data regarding the sample may also be uploaded to a memory storage component of the cassette; such the sample is uniquely identified therein. Alternatively, a unique identification string of the device 230 could be downloaded to a computing device and associated with data relating to the sample therein. Yet alternatively, an embodiment wherein the identity of the cassette or sample would be marked by an inscription, printing or barcode are also contemplated. Then, the physician would re-seal the interface 233 with tape 234, if present, and deposit the sample in a fixation solution.

Alternatively to the above, the activation of the data logging device 230 could proceed automatically. For example, the device could be activated by detecting the change in conductance of its environment upon immersion into the fixative. Otherwise, the device could be activated by a standard manipulation of the cassette involved in the above process— e.g., the cassette could be configured such that the closing of the cover member 219 would create or break a specific electrical connection, thereby activating the device 230.

System Comprising a Tissue Sample Holder Connected to a Lid

Figure 24A:
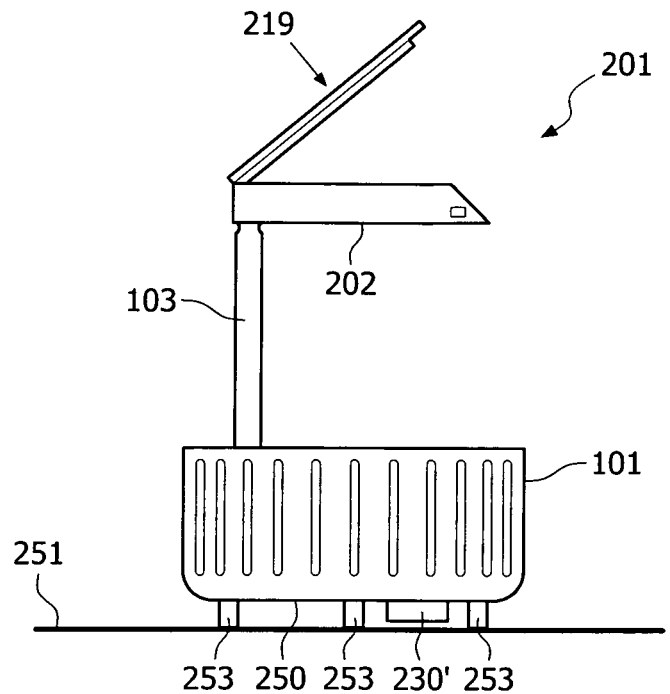
FIG. 24a illustrates an embodiment of a system according to the present invention.
Figure 25:
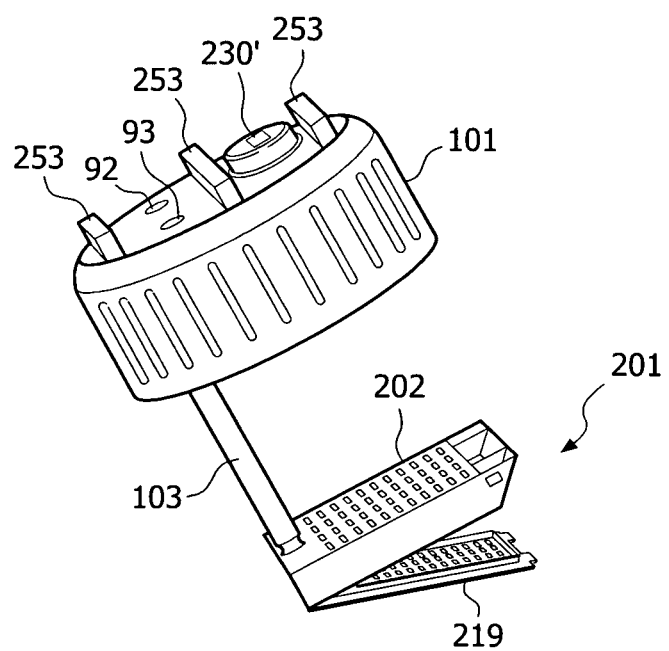
FIG. 25 illustrates another embodiment of a system according to the present invention.
Figure 26A:
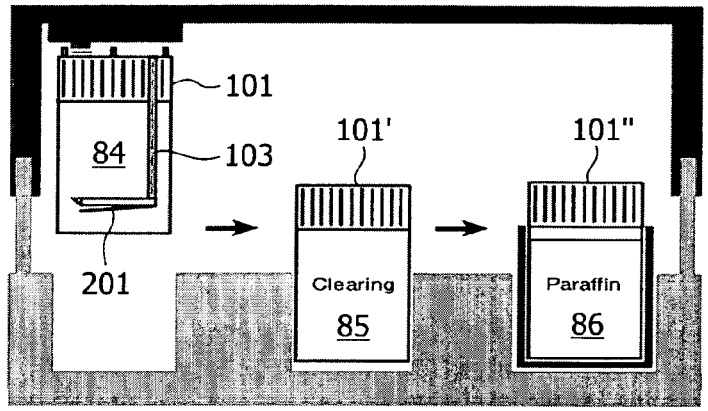
FIG. 26 is a schematic representation of the sequence of steps performed for preparing a tissue sample. Steps A-C represent the positioning of vial according to the invention containing a sample that has been fixed, dehydrated and initially cleared using a FCD solution in a processing instrument according to the invention. Steps D-E represent dehydration and final clearing of the sample by transferring said sample to a suitable vial containing a suitable dehydrating-clearing solution. Steps F-G represent the infiltration of the sample with an inert specimen matrix by transferring said sample to a suitable vial containing a suitable matrix, e.g. paraffin.
Figure 26B:
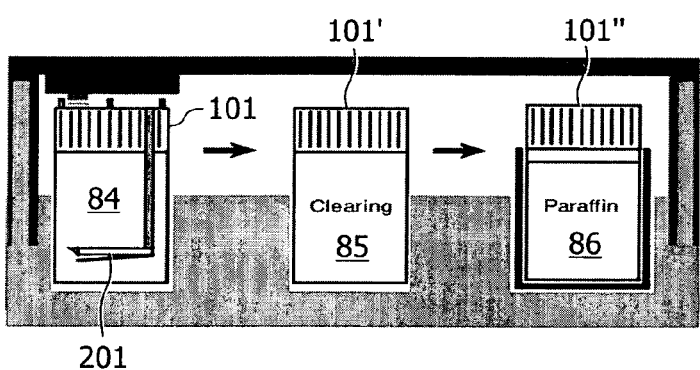
Figure 26C:
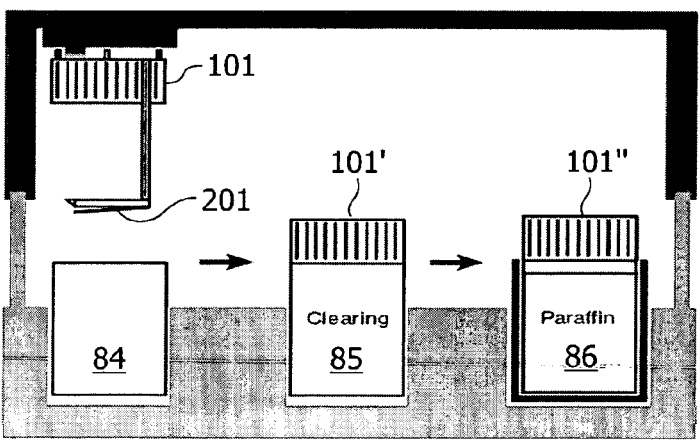
Figure 26D:
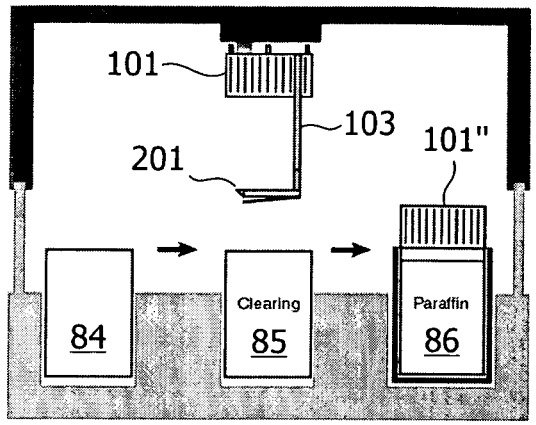
Figure 26E:
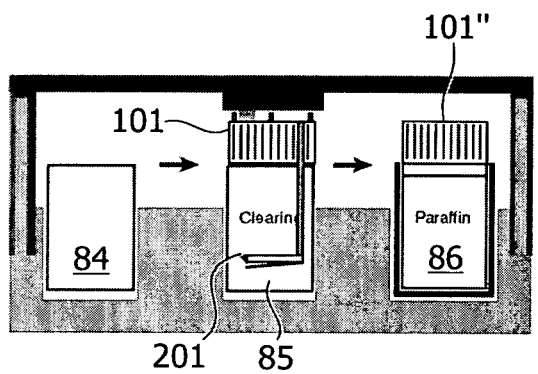
Figure 26F:
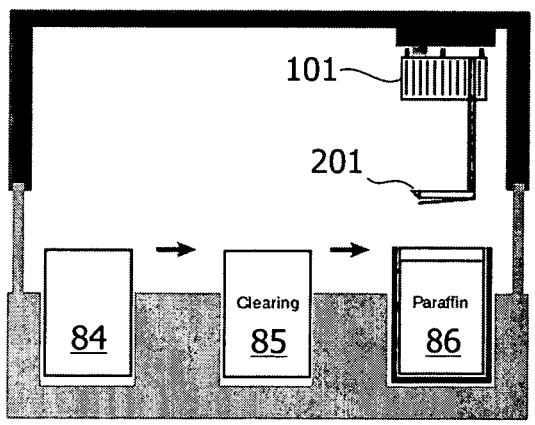
Figure 26G:
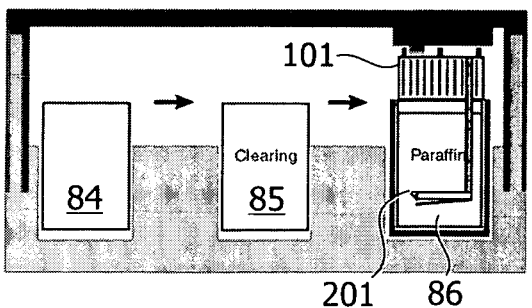

Referring to FIGS. 24a and 25, preferred embodiments of a tissue sample holder connected to a lid according to the invention are illustrated. In use a sample is deposited in a sample holding cassette 201, which is joined with the resealable cover 101 of the first vial, e.g., via an elongated member 103. In FIGS. 24a and 25, the data logging device 230' is provided on the lid 101.

Figure 24B:
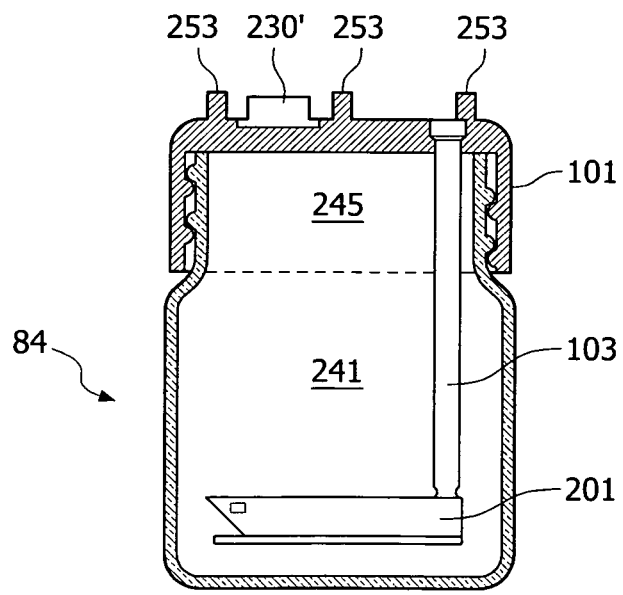
FIG. 24b illustrates another embodiment of a vial and a system according to the present invention.

In FIG. 24a the top side 250 of the resealable lid 101 is adapted to stably rest on a support 251, for example by means of suitable number of legs 253. In this configuration the tissue cassette is easily accessible and a sample can be easily introduced in the cassette. Advantageously, using such arrangement, once introduced in the cassette, a user will not have to manually touch the tissue sample. Hereupon, the tissue processing cassette is closed and a physician may turn the resealable lid 101 upside down and position this onto the top opening 245 of a vial body 241 (FIG. 24b). The vial may comprise a first processing solution, such as a solution comprising a fixative, such that the sample placed in the sample cassette 201 and entering the interior space of the vial as shown in FIG. 24b, and will become submerged into the solution. At that time a physician may activate the measurement of time and temperature by the data logging device 230', which is in this embodiment easily accessible on the top side of the lid 101.

Vial Containing Said Tissue Sample Holder Provided with a Data Logging Device

In another embodiment, the invention relates to a vial configured to receive and retain liquids therein and a tissue sample holding means for securing a tissue sample therein. The vial further comprises a data logging device capable of registering and transmitting data regarding the sample and conditions wherein said sample is processed. Preferably, said data logging device comprises the elements and functions as enumerated above.

In one embodiment the tissue holding means may be loosely deposited within, i.e., not in an attached or joined relation with, the vial. Advantageously, this may allow a user to choose any tissue holding tool, such as preferably any tissue processing cassette, which may be simply deposited within the vial to compose the present system.

In another embodiment, the tissue holding means may be provided attached to or joined with the vial. Such relationship may be advantageously configured to effect the submersion of the sample holding means, and therewith the tissue sample contained therein when using the system, into a solution present in the vial. Such relationship may also limit the movement, e.g., swaying or swirling movements, of the sample holding means inside the vial upon processing, thereby protecting the integrity of the sample.

FIG. 24b illustrates a vial 84 having a hollow body 241 configured to receive and hold liquids, i.e., having walls impermeable to the said liquids. The vial 84 may further comprise a resealable lid 101 configured to fittingly and reversibly seal the top opening of the vial 84. A sample holding means may be attached to or joined with the body 241 of the vial 240, typically to the inner surface of the base or sidewalls, or alternatively may be attached to or joined with the resealable lid 101 of the vial typically to the surface of the lid configured to face the internal space of the vial when placed thereon. FIGS. 11 and 24b show embodiments in which the tissue holding means, respectively, a clasping-arm arrangement 111, 112 or a tissue processing cassette 201, is joined to the resealable lid 101 via an elongated member 103. Such elongated member 103 may serve to suitably position the sample holding means within the inner space 241 of the vial 84, such that this would become immersed in solutions introduced thereto, advantageously by being placed, e.g., in the lower half, lower third, lower fourth of the body of the vial, or otherwise adjacent or closely proximal to the base of the vial.

A typical operation of this system may be as follows. The tissue sample to be processed is secured in the tissue sample holding means, which is then deposited within the vial. As mentioned above, in usual histology applications, the isolated tissue sample may be preferably submerged in a first solution comprising a fixating agent substantially immediately after its dissection. Hence, the vial in which the sample holding means comprising the tissue sample is deposited may be provided with such suitable first solution. The data logging device, which may have functionality analogous to that described elsewhere in the application, is then be activated to record the temperature of its surrounding environment and time, thereby yielding data points of temperature vs. time. Also as described elsewhere in this application, the measured data may be written to a memory storage component, which may be preferably provided on the vial, and even more preferably may be an integral part of the data logging device, or may alternatively be externally provided.

The data logging device according to the present invention can be placed on several positions. The data logging device may be provided on or inside the vial, on the lid of the vial, or on the elongated member 103—if present—or on the tissue sample cassette (see above).

In one embodiment, the data logging device is provided on the vial. Depending on the placement of the data logging device, the latter may become immersed in the same solution in which the tissue sample deposited in the vial is submerged. For example, to achieve the said submersion, the data logging device may be provided on or attached to an internal surface of the vial, and may preferably be located adjacent to the surface of the vial which normally represents a base, such as to ensure submerging of the data logging device even with relatively little liquid present in the vial.

Alternatively, the data logging device may be provided on the vial such that it would not be contacted with solutions deposited within the vial. For example, when provided on an interior surface of a vial, it may be vertically upwardly sufficiently distanced from the base of the vial, such as to avoid exposure even when the vial is filled with a common amount of fluid. Alternatively, the data logging device may be provided on an external surface of the vial such that it faces the ambient environment surrounding the vial rather than being exposed to the vial's interior.

The present inventors have realised that in typical applications the heat exchange between solutions deposited within the vial and the environment surrounding the vial through the walls of the latter can sufficiently equilibrate the temperatures between the solution present in the vial and the vial's surroundings, such that a temperature reading taken by a data logging device not immersed in the solution, or even facing the exterior of the vial, is sufficiently representative of the temperature of the said solution. Moreover, a user may exercise care when, e.g., immersing a tissue sample to a fixative in a vial with a data logging device provided on the external surface, so as to ensure that the fixative has been previously equilibrated to the same temperature as the vial, e.g., room temperature. Provision of the data logging device on the exterior walls of the vial may simplify the accessibility and manipulation thereof, especially if the device does not communicate wirelessly. Yet in another embodiment, a data logging device placed outside of the said solution may comprise a thermal probe configured to extend into the said solution, to directly measure the temperature thereof.

Position of the data logging device on the vial entails several advantages. For example, provision of the data logging device on the vial may allow configuring the system with any tissue sample holding means commonly used in the art, such as a tissue processing cassette. Therefore, the user may be relatively free to use his preferred type of tissue sample holding means in conjunction with the present system. Moreover, in this embodiment, the data logging device may be provided so as not to come in contact with liquid compositions used in the processing. Therefore, the use of data logging devices with less liquid resistance may be possible.

In another embodiment, the data logging device is provided on the lid. In FIGS. 24a and 25 for instance it is illustrated that data logging device 230' is provided on the lid 101. In this manner, the sample can be moved between vials by moving the lid 101 joined to the sample holding means 201 between the different vials, whereby the data logging device 230' remains in association with the sample throughout the procedure.

In yet another embodiment, the data logging device is provided on the tissue sample cassette (see also above). Such embodiment involves a number of advantages. Data measured by the data logging device remains in an unambiguous association with the processed sample through their physical association. Data concerning the sample deposited to the sample holding means may be recorded, e.g., on the sample holding means, such as to an electronic memory storage provided thereon or by inscription. Alternatively, the sample holding means may be provided with a unique ID string, such as an electronic ID, a bar code, or an inscribed ID, which is associated with the respective data in an external database. Yet, later on, data collected by the data logging device may be also uploaded into such external data storage device, and associated with the unique ID of the sample.

In another embodiment, after completing the respective treatments, the physical connection between the elongated member 103 and the tissue cassette 201 may be broken allowing further processing of the sample apart from the lid. In such case the identity association would be preserved, uniquely linking these components. Advantageously, when the tissue cassette 201 is used, the memory storage component may be provided on the base member 202 thereof, which, as common in the art may be subsequently used as a support for mounting the sample into a paraffin block (explained elsewhere in the application). Thereby, the unique identification would be extended all the way to the tissue block.

In yet another advantageous development, the memory storage component present in such cassette may be used to upload the respective data relating to the nature of the sample or recorded by the data logging device 230, 230', thereby providing for eventual association of the data directly with the tissue block, e.g. using the system according to FIG. 23 and explained elsewhere.

Use of the Registered Data

As explained above, a particularly useful application of the invention which allow for registering data relating to identity and processing of tissue samples is to allow for better monitoring of the processing steps involved in this process, and particularly to obtain reliable information about the time that has passed before the sample—routinely kept in a fixative solution after dissection—has entered a histology laboratory and about the temperatures to which the sample has been exposed during that time.

The histology laboratory may analyse the data recorded by the data logging device based to decide about further processing of the sample.

For example, the analysis may involve determination of the total time during which the sample has been exposed to a fixative. In one instance, if the time has passed some cut-off value, the histology laboratory may proceed with the subsequent processing steps, irrespective of the development of temperature during that time.

Otherwise, the analysis may involve the determination of an integral sum of the temperature as a function of time. Once again, if such integral value has passed a pre-decided value, the sample may be forwarded directly to further processing steps. Conversely, if the integral value is below a certain cut-off value, the histology laboratory may decide to continue fixation and calculate the time needed to completely fix the tissue.

Such cut-off values may depend on various parameters which the histology laboratory may optimise empirically, such as the type of tissue, type and concentration of fixative, etc.

Since histology laboratories for the remaining processing steps usually follow strict protocols, it may not be needed to use the data logging device to record conditions, such as time and temperature, during such steps. On the other hand, such logging may be continued during subsequent steps, which may provide a more complete history of processing of a particular sample, and provide checks for the procedures of the histology laboratory, which may be consulted if the said sample produces unusual results.

In a preferred embodiment, the sample may be placed into a processing station, e.g., into a processing station essentially as illustrated in FIG. 8 or 12 and explained elsewhere in this application. The vials adopted for such processing station may involve further requirements, such as the presence of breakable septa, which are thoroughly explained in this application and may be easily applied to vials of the present aspect comprising the data logging device.

In an alternative embodiment, as shown in FIG. 26 the processing station may actuate the transfer of the resealable lid 101 and its associated tissue holding means 201 with the sample enclosed therein, joined by the extended member 103, between different vials 84, 84', 84" positioned substantially horizontally with respect of each other. For example, once a suitable means of the processing station, such as a reader linked to a robotic arm, has queried the data logging device on the lid of a vial 84 (step b) and the station decided on continuing the treatment, a robotic arm may suitably grasp and transfer the lid 101 (step c) with the associated sample holding means 201, between a series of vials 84', 84", covered with protecting lids 101', 101", containing processing solutions, e.g. clearing and paraffin-rich solution such as those disclosed in the present application (steps c-g).

Preferably, the vial receiving means of such processing station may comprise a suitable reader means adapted to read the data stored by the data logging device of the vial. Such data is downloaded to a computing device, which may store it, use it in necessary algorithms and/or upload it to another memory storage component. Such reader may comprise an interface provided on the vial receiving means of the processing station, which is configured to engage with a co-operating interface of the data logging device, when the vial is placed in the station. In the embodiments, the processing station may query the information stored on the data logging device through its respective interface. Alternatively, the communication may be wireless.

Advantageously, the processing station may comprise or may be connected to analysis components which analyses the said data and may decide on the further treatment of the sample. For example, such decision may involve further fixation in the same or another fixative for a particularly calculated time and at a certain temperature, or forwarding the sample to further processing, such as by exchanging of the liquids in the vial, as explained extensively in this application. Data Another aspect of the present invention is a tissue sample processed according to the method of the present invention. The sample can be distinguished from samples of the prior art because both cellular morphology and immunohistochemical profile are preserved, while degradation and modification of nucleic acids is limited.

Another aspect of the present invention is the data obtainable from a sample processed according to the method of the present invention. The data may be micrograph 2D or 3D (virtual) images of sections, morphological analysis data, nucleic acid concentration and integrity data and data from downstream nucleic acid analyses. The preserved sample may be prepared for nucleic acid analysis, or nucleic acid extracted from the sample using any suitable protocol known to those skilled in the art, e.g. Proteinase K digestion, followed by mild extract.

EXAMPLES

The following examples demonstrate the utility of the present invention. The described examples make use of fresh human surplus and experimental animal tissues or living cells in suspension. The methods and compositions of the current invention are applicable for tissue preservation for histopathological and molecular biological analysis for a broad range of animal (including human) and plant species. The examples are included to demonstrate preferred embodiments of the invention. However, the practice of the invention is not limited or restricted in any way by them.

Example 1

Exemplary General Manner of Tissue Processing

Tissue samples to be processed according to the current invention should be processed as quickly as possible after excision from the source after the onset of ischemia or death, or after removal from the soil or any other substrate solution or medium. In the case the samples posses a protective barrier that would interfere with FDC diffusion (e.g. a renal capsule or the waxy coating of plant material) this barrier should be removed prior to proceeding with the processing as described in the current invention. Large samples should be dissected/laminated into smaller fragments to maximize FDC diffusion in the first step of the present method. A general rule of thumb states the tissue thickness should not exceed 5 mm in at least one spatial dimension to allow proper fixation (Kieman J P: Histopathological and Histochemical Methods, Theory, and Practice, ed 3. Oxford, Butterworth-Heinemann, 1999). Samples that consist of cell cultures should be carefully scraped from the culture flask and/or poured into a centrifuge tube. After centrifugation, a fibrin clot is generated that functions as a meshwork that keeps the cells in place. Once the specimen (artificial cell block, animal, human or plant tissue) is suitably fixed, dehydrated, cleared and infiltrated with ISM, it can be embedded in a casting ISM block according to the routine pathology laboratory procedures. The tissue samples treated according to the procedures described in the current invention, can be sectioned in an excellent manner, according to the routine procedures followed in a pathology laboratory (section thickness ranging from 3 µm to 30 µm). None of the following sectioning problems occur with specimens processed according to the method of the invention: embedding blocks are too soft or too hard and therefore difficult to section, indentation of the tissue in the ISM used to make the tissue block due to incomplete tissue dehydration, sections that tear, crumble or display striae, tissue ribbons that fail to form or are deformed. Section adhesion to glass slides is comparable to that of standard FFPE tissue sections and is accomplished by placing the slides overnight at 37 deg C. or for shorter periods at higher temperatures. The deparaffination procedures as employed for FFPE can be used on sections made from tissues processed according to the described invention. After deparaffination, the tissue sections can be rehydrated and used for histological or immunohistochemical staining, or processed directly for nucleic acid analysis. Advantage of the described method is that it will not cause a drastic reordering of the workflow in pathology laboratories (FIG. 1). Standardization of tissue fixation and processing using the described invention will ease comparison of specimens from different laboratories, this is of particular importance if samples collected at different local sites will be analyzed in a reference laboratory.

Example 2

The Tissue Morphological Detail and Cytology of Tissues Processed According to the Current Invention is as Good as or Better than FFPE Tissues (e.g. Prostate Tissue and Bronchoscopic Biopsy)

A prerequisite for the general acceptance and introduction of the current invention into routine pathology, research and clinical laboratories is that tissues processed according to the described invention have a morphology comparable or superior to the one of FFPE tissues.

Figure 2:
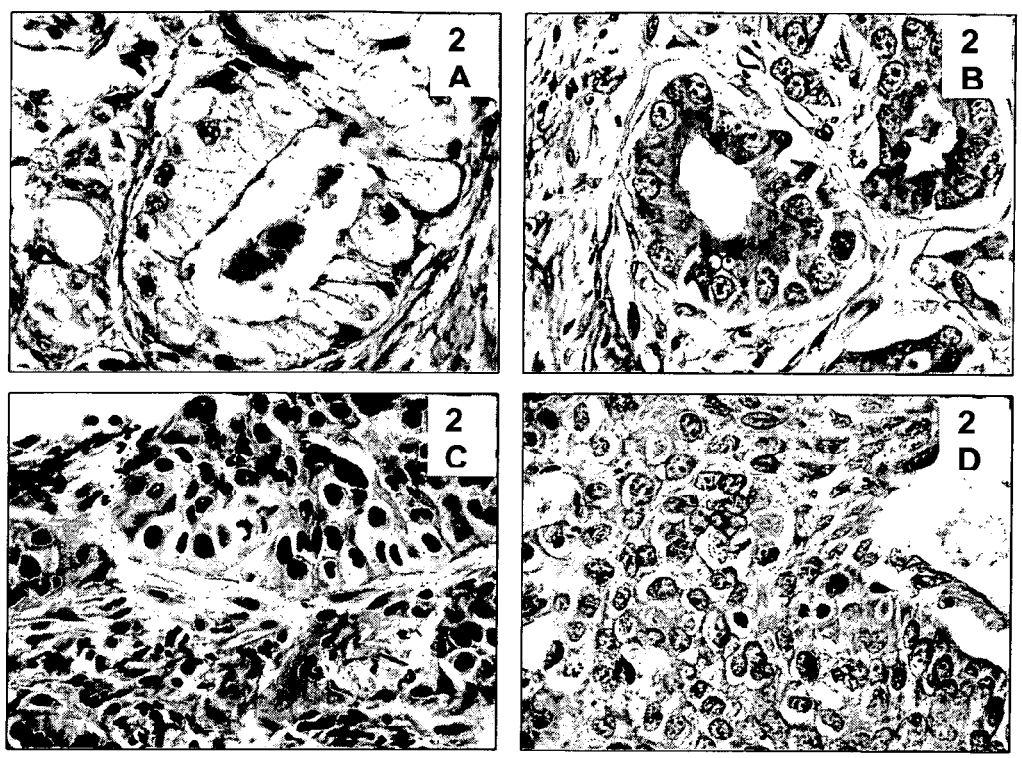
FIG. 2 shows the comparison between the tissue morphology of prostate tissue and a bronchus biopsy processed according to standard procedures (FFPE) and according to the described invention. The sections are stained with haematoxylin phloxine.

Typical examples that demonstrate the importance of preservation of good morphological detail for histopathological diagnosis are prostatic and bronchoscopic biopsies. Prostatic (FIGS. 2A and 2B) and bronchoscopic biopsies (FIGS. 2C and 2D) are shown. FIGS. 2A and 2C show biopsies processed according to standard routine pathology procedures (4% formalin fixation for 16 hours at room temperature, followed by tissue processing in a Leica Tissue Processor). FIGS. 2B and 2D show biopsies processed according to the procedures described in the current invention. There are no differences in sectionability between the routine FFPE blocks and paraffin blocks prepared according to the described invention. Both types of sections were automatically deparaffinized and stained with Hematoxylin Phloxin Saffranin according to routine procedures.

The prostatic biopsy (FIGS. 2A and 2B) contains tumoral glandular structures. The cytological detail of the tumor cell nuclei is characterized by the prominent nucleoli. The recognition of these cytological details is superior in the biopsy processed according to the procedures described in the current invention (FIG. 2B). The bronchoscopic biopsies (FIGS. 2C and 2D) contain a squamous cell carcinoma. The cytological detail of the tumor cell nuclei and mitotic figures is superior in the biopsy processed according to the procedures described in the current invention (FIG. 2D).

Example 3

Immunohistochemical (IHC) Stainings Performed on Tissue Processed According to the Described Invention and Embedded in Paraffin The antigenic profile of the samples processed according to the current invention should be comparable to the one of FFPE tissues. In addition, the antigen retrieval procedures that are applied to FFPE tissues should be applicable without any (or only minor) adaptations on material processed according to the described invention. Table 1 lists 85 antibodies (both monoclonal and polyclonal) that have been applied successfully on human surplus tissues processed according to the described invention. In total, 4239 sections were stained immunohistochemically and evaluated by pathologists, who found no differences between standard FFPE sections and sections from tissues processed according to the current invention. Data is shown in Table 1.

TABLE 1

| Antibody target | Number of IHC stainings performed | Type of antibody |
|---|---|---|
| -1-antitrypsin | 10 | P |
| -actin, sarcomeric | 6 | M |
| -smooth muscle actin | 27 | M |
| AFP | 10 | P |
| ALK | 13 | M |
| BCL-2 | 101 | M |
| Calcitonin | 1 | P |
| Calretinin | 36 | P |
| CD1 a | 8 | M |
| CD10 | 83 | M |
| CD138 | 46 | M |
| CD15 | 64 | M |
| CD20 | 218 | M |
| CD23 | 19 | M |
| CD3 | 194 | M |
| CD30 | 131 | M |
| CD31 | 24 | M |
| CD34 | 16 | M |
| CD4 | 9 | M |
| CD45RB | 173 | M |
| CD5 | 73 | M |
| CD68 | 64 | M |
| CD79a | 21 | M |
| CD8 | 7 | M |
| CD99 | 3 | M |
| CEA | 159 | M |
| Chromogranin | 2 | M |
| Chromogranin A | 53 | M |
| CK1, 5, 10, 14 | 171 | M |
| CK14 | 83 | M |
| CK2, 5, 6, 8, 15, 18, 19 | 98 | M |
| CK20 | 135 | M |
| CK5, 6 | 37 | M |
| CK7 | 248 | M |
| CK8 | 106 | M |
| CMV | 12 | M |
| Cyclin D1 | 26 | M |
| Desmin | 16 | P |
| E-cadherin | 14 | M |
| EBV-LMP1/CS 1-4 | 15 | M |
| EMA | 213 | M |
| ER | 216 | M |
| GFAP | 29 | P |
| Glycophrin C | 2 | M |
| HAM56 | 1 | M |
| Helicobacter | 19 | P |
| HepBcAg | 32 | P |
| HepBsAg | 37 | P |
| HMB45 | 15 | M |
| HPV | 1 | P |
| HSV1 | 8 | P |
| HSV2 | 6 | P |
| KAPPA | 19 | P |
| Ki-67 | 2 | M |
| Lambda | 19 | M |
| Lysozyme | 2 | P |
| Mycobacteria | 67 | P |
| Myeloperoxidase | 8 | P |
| Myoglobin | 1 | M |
| Neu | 336 | P |
| Neurofilament | 13 | M |
| NSE | 30 | M |
| p53 | 9 | M |
| PCNA | 2 | M |
| *Pneumocystis carinii* | 16 | M |
| PR | 218 | M |
| PSA | 37 | P |
| PSAP | 33 | P |
| S100 | 80 | P |
| Synaptophysin | 2 | M |
| Synaptophysin | 36 | P |
| Tdt | 3 | M |
| Thyroglobulin | 6 | P |
| TTF-1 | 112 | M |
| Ubiquitin | 19 | P |
| Vimentin | 37 | M |
| CD117 | 8 | P |
| CD57 | 2 | M |
| CD18 | 1 | M |
| Collagen type IV | 1 | P |
| Fibrinogen | 2 | P |
| HCG | 1 | P |
| Myf-4 | 1 | M |
| Myoglobin | 2 | P |
| PLAP | 3 | M |

P = polyclonal
M = monoclonal

Example 4

FDA-Approved HER-2 Immunostaining of Human Surplus Segments of Breast Tumor Biopsies, Processed According to the Current Invention A surplus breast cancer sample was prepared using a method of the present invention. It was incubated in FDC solution comprising 10% (v/v) formaldehyde, 65% (v/v) methanol, 5% (v/v) acetic acid and 20% (v/v) diethylether. The surplus sample was subsequently treated with clearing solution comprising diethylether, and then embedded in molten paraffin at 52 deg C.

Figure 3:
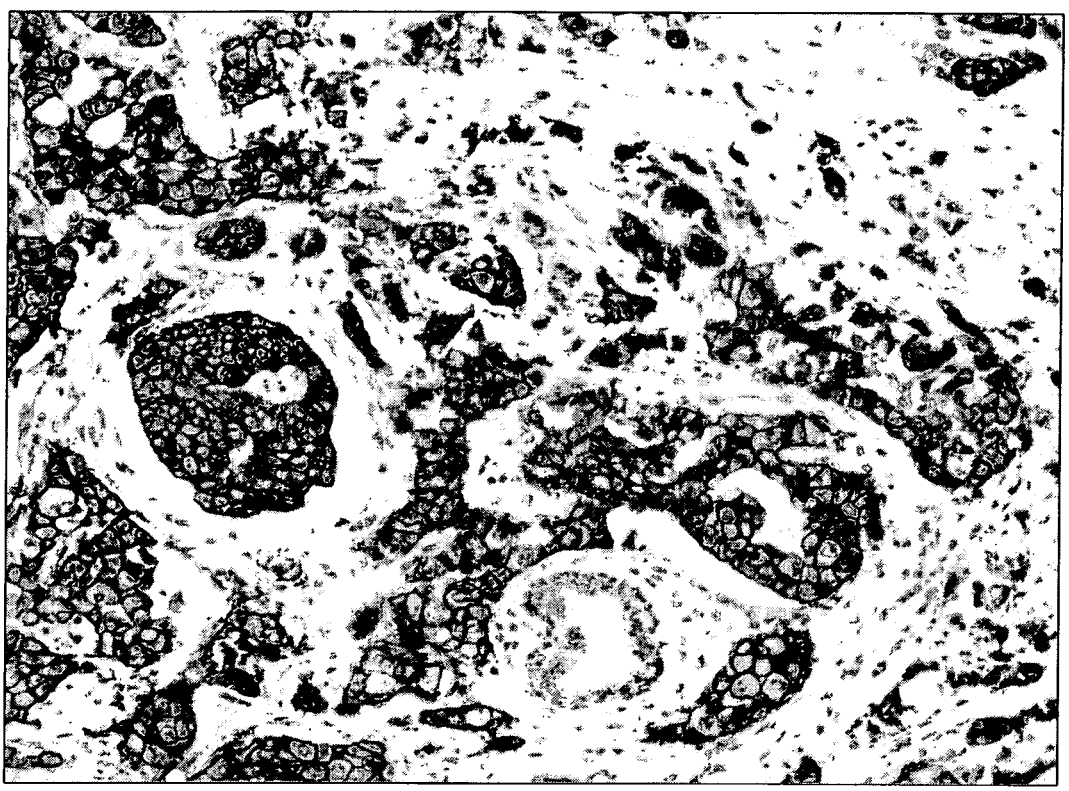
FIG. 3 shows a FDA-approved HER-2 immunostaining performed on a breast tumor biopsy, processed according to the procedure as described in the invention.

There were no differences in sectionability between the routine FFPE blocks and paraffin blocks prepared according to the described invention. Pathologists found the morphological quality of the tissue samples processed according to the described invention to be good to very good. IHC stainings for hormone receptors and the growth factor receptor HER-2 could be performed with the protocol described for standard FFPE tissues. FIG. 3 shows a strong membrane staining for HER-2 (chicken wire pattern) which indicates score 3+. This result was similar with the result obtained on the FFPE sample of the same tumor. This is important as the HER-2 immunodetection is an "FDA-approved test". This means that every important alteration/adaptation of the staining procedure would invalidate the test.

Example 5

Figure 4:
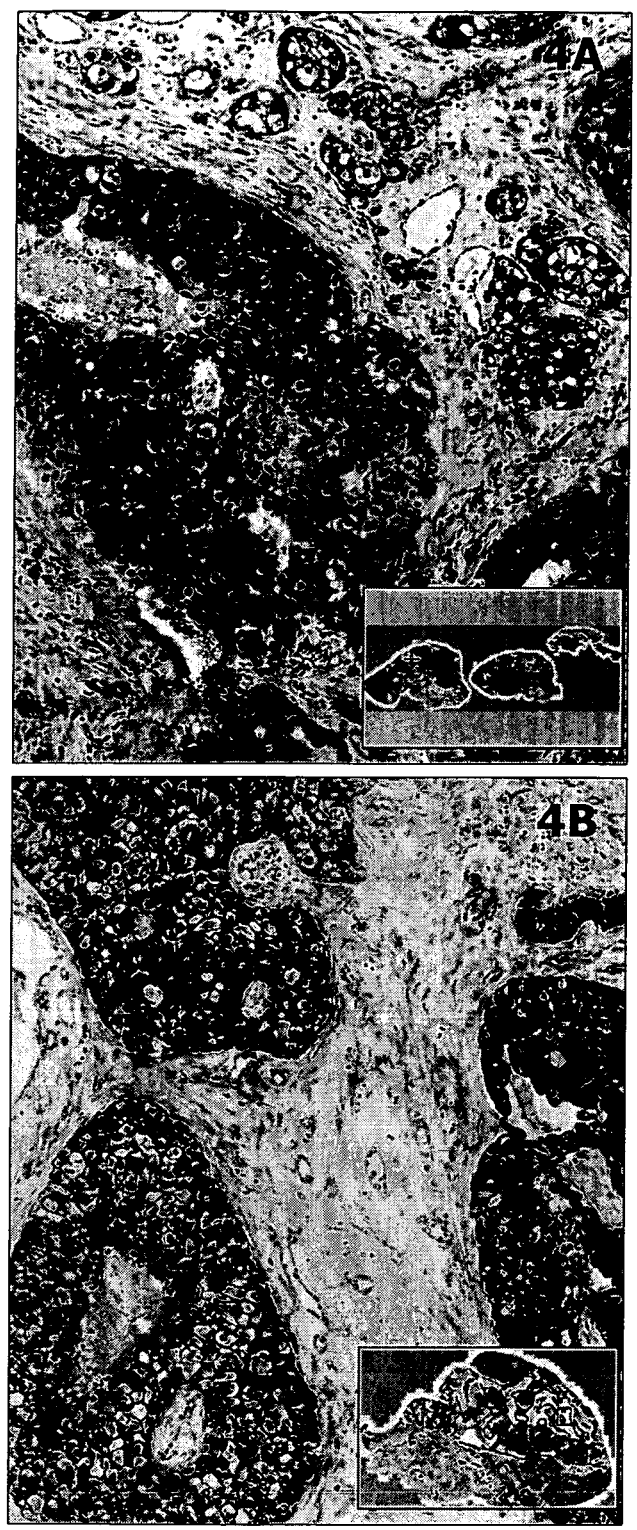
FIG. 4 shows immunohistochemical staining of phosphorylated AKT (pAKT), performed on breast tumor specimens: comparison of FFPE tissue and specimens processed according to the current invention.

IHC Staining of Antigens that are Very Sensitive for Fixation Artifacts E.g. Phosphoproteins and/or Phosphorylation-Sites can Also be Performed on Sections Prepared According to the Methods of the Invention Commercial phosphorylation state-specific antibodies are available for more than 300 different phosphoproteins and/or phosphorylation-sites (Mandell J W: Phosphorylation state-specific antibodies. Applications in investigative and diagnostic pathology. Am J Pathol 163: 1687-1698, 2003). Important here is the transient nature of the phosphorylation state, since protein phosphorylation is a very dynamic process. It has been shown that post-mortem conditions and tissue resection, can influence the phosphorylation state (Song J, Combs C K, Pilcher W H, Song L Y, Utal A K, Coleman P D: Low initial tau phosphorylation in human brain biopsy samples. Neurobiol Aging 18: 475-481, 1997). In addition, it seems that for some phosphoproteins e.g. pERK, the diffusion of formalin is too slow to maintain the phosphorylation state in the core of the biopsy. The composition of FDC is such that it allows the investigation of the phosphorylation state. As is demonstrated in FIG. 4, pAKT immunostaining of FFPE breast tumors and bronchus biopsies results in diffuse cytoplasmic signals (FIG. 4A), while pAKT staining of breast tumors and bronchus biopsies processed according to the current invention results in crisp membrane signals (FIG. 4B).

Example 6

Figure 5:
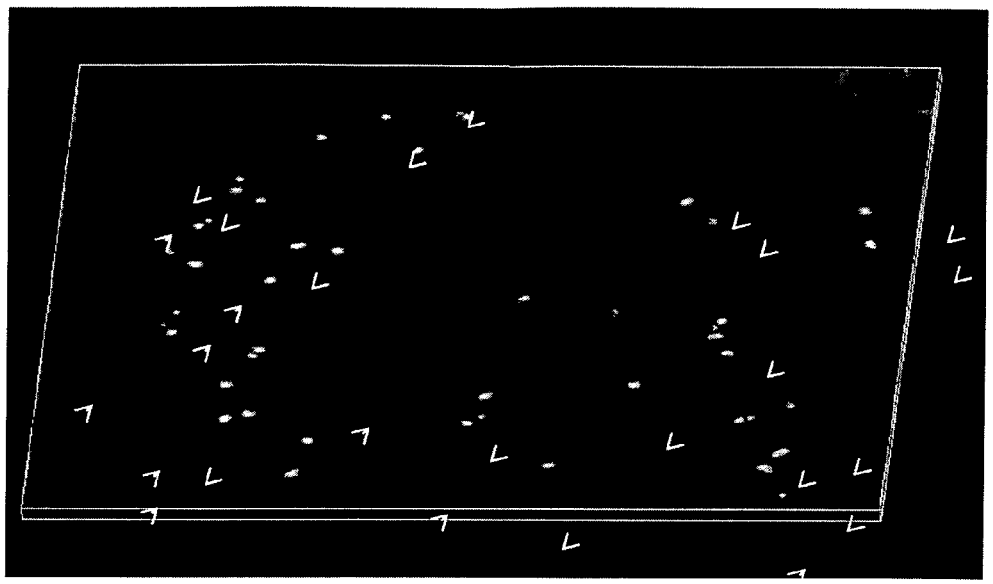
FIG. 5 shows fluorescent in situ hybridisation (FISH) for the HER-2 gene performed on a breast tumor specimen processed according to the current invention.

Fluorescent In Situ Hybridisation (FISH) can be Performed on Sections Prepared According to the Methods of the Invention Target retrieval techniques such as heating and proteinase K digests are current tissue pre-treatment practice for FISH detection of genes on FFPE samples. In our hands, the variations that occur during the pre-analytical phase (use of different formulations of formalin, different fixation times, different dehydration and embedding procedures, . . . ) necessitate sample-to-sample optimisation of the section pre-treatment. FISH for the HER-2 gene (FDA-approved test) can be performed on sections prepared according to the methods of the invention. Data is shown in FIG. 5 which depicts a section of breast tumor sample processed according to the method of the present invention in which HER-2 gene is indicated. Data shows a higher signal/background ratio and a broader fixation window.

Example 7

Figure 6:
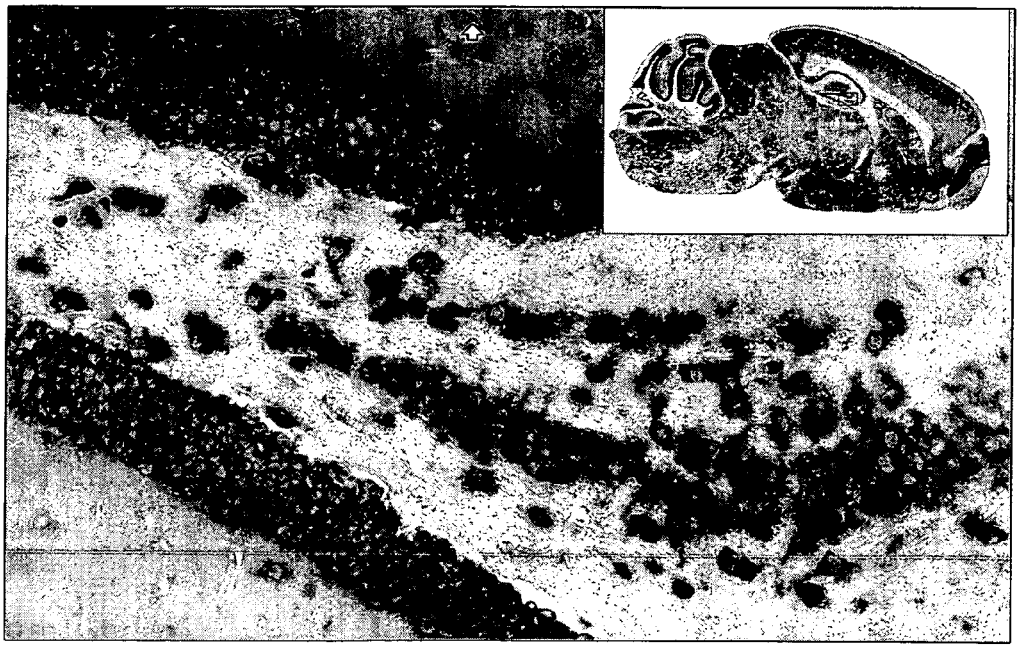
FIG. 6 shows a chromogenic in situ hybridisation (ISH) for 28S rRNA on a mouse brain processed according to the current invention. Hybridisation signals were demonstrated with standard alkaline phosphatase nitroblue tetrazolium salt/5-bromo-4-chloro-indolyl phosphate (NBT/BCIP) detection.

Chromogenic In Situ Hybridisation (ISH) can be Performed on Tissues Processed According to the Described Invention without Adaptations of the Hybridisation Protocol Used for FFPE Tissues ISH was performed for 28S rRNA on a mouse brain processed according to the method of the current invention. Hybridisation signals were demonstrated with standard alkaline phosphatase NBT/BCIP detection. Data is shown in FIG. 6. In the hippocampal region of the mouse brain, the cytoplasm of nerons in hippocampus and gyrus dentatus shows strong hybridisation signals.

Example 8

Figure 7:
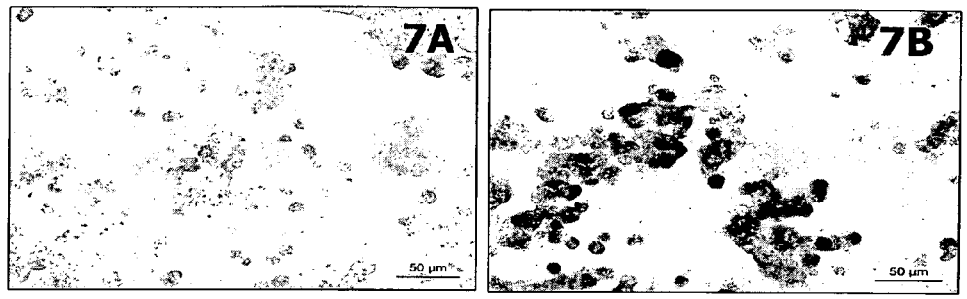
FIG. 7 shows that a chromogenic ISH can be performed on an artificial tissue cell block prepared from a transfected cell line according to the described invention. ISH was performed for the transcript encoding for the transfected protein. Hybridisation signals were demonstrated with standard alkaline phosphatase NBT/BCIP detection.

Chromogenic ISH can be Performed on Artificial Tissue Cell Blocks Prepared from Transfected Cell Lines According to the Current Invention ISH was performed for the transcript encoding the transfected protein. Hybridisation signals were demonstrated with standard alkaline phosphatase NBT/BCIP detection. Sections prepared according to the described invention are shown in FIG. 7. Sections (FIG. 7A) are completely negative after hybridisation with the sense (negative control) probe and clear-cut hybridisation signals (FIG. 7B) are obtained with the antisense probe.

Example 9

Total RNA can be Extracted from Paraffin Sections Prepared According to the Method of the Described Invention Two sections (10 μm thickness) of a rat liver tissue block processed according to the current invention were made nuclease-free, using disposable blades. The tissue block was prepared according to the present invention as described in Example 1. All following procedures were performed under nuclease-free conditions. The sections were collected in nuclease-free tubes, deparaffinized, and the remaining tissue was washed in isopropanol. The tissue was subsequently digested for 3 hours with proteinase K and the digested tissue components were ethanol-precipitated. The precipitated cell components were then resuspended and homogenized in a highly denaturing guanidine isothiocyanate-containing buffer, which immediately inactivates ribonucleases to ensure the isolation of intact RNA. Synthetic nucleic acid, in the form of polyinosinic acid, is added as carrier material to reduce loss of RNA during the extraction procedure. Ethanol is then added to provide appropriate binding conditions, and the sample is then applied to a silica-based membrane in spin column format. The total RNA binds to the column and contaminants are washed away. The RNA is then eluted in nuclease-free water. A kit that can be used for the RNA extraction is e.g. the RNeasy Mini or Micro kit from Qiagen (Hilden, Germany).

Figure 13:
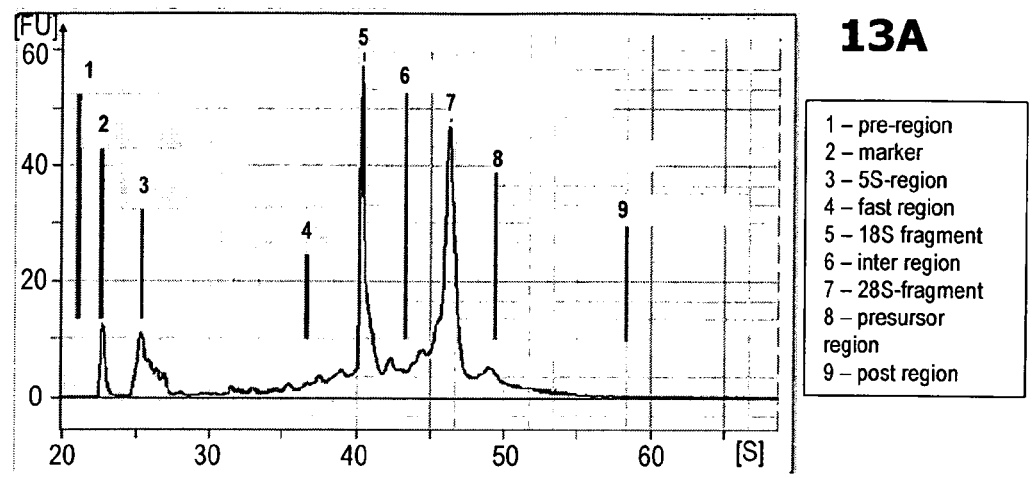
FIG. 13 shows an explanatory scheme of a total RNA BioAnalyzer profile, an example of a total RNA profile from intact RNA isolated from experimental rat liver cryosections and an example of a total RNA profile from RNA isolated from rat liver paraffin sections prepared according to the current invention.
Figure 13:
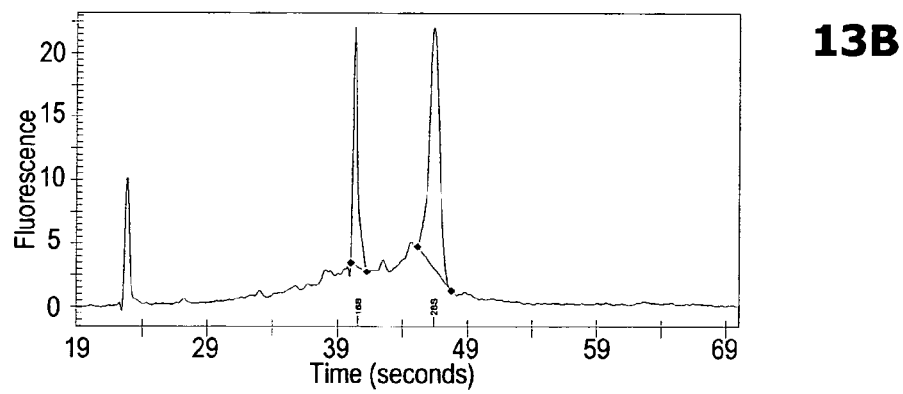
Figure 13:
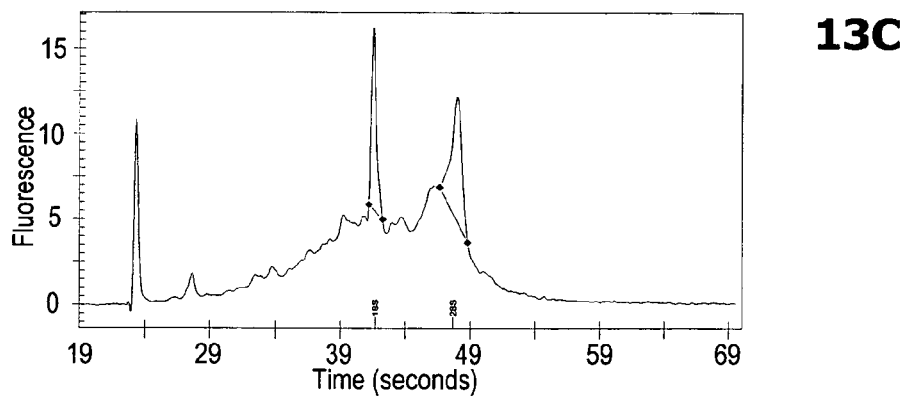

The assessment of RNA integrity is a critical first step in obtaining meaningful gene expression data. Using intact RNA is a key element for successful microarray or RT-PCR analyses. The Agilent 2100 bioanalyzer and RNA LabChip® kits were used for the determination of RNA quality. Profiles generated on the Agilent 2100 bioanalyzer yield information on concentration, allow a visual inspection of RNA integrity, and generate ribosomal ratios. The bioanalyzer software generates both an electropherogram and gel-like image. The electropherogram provides a detailed visual assessment of the quality of an RNA sample. An example of such a total RNA profile with its different subregions is shown in FIG. 13A. Previously, researchers have used the ribosomal ratio in both slab gel analysis and as a feature within the bioanalyzer software to characterize the state of RNA intactness. Slab gel analysis of total RNA samples using ribosomal ratios often results in an inaccurate assessment of the RNA integrity. The Agilent 2100 bioanalyzer provides a better assessment of RNA intactness by showing a detailed picture of the size distribution of RNA fragments (FIG. 13A). RNA degradation is a gradual process. As degradation proceeds, there is a decrease in the 18S to 28S ribosomal band ratio and an increase in the baseline signal between the two ribosomal peaks and the lower marker. The RNA Integrity Number (RIN), was developed to remove individual interpretation in RNA quality control. Using this tool, sample integrity is no longer determined by the ratio of the ribosomal bands alone, but by the entire electrophoretic trace of the RNA sample (FIG. 13A), including the presence or absence of degradation products. In this way, interpretation of an electropherogram is facilitated, comparison of samples is enabled and repeatability of experiments is ensured.

A BioAnalyzer RNA profile from intact total RNA isolated from experimental rat liver cryosections is shown in FIG. 13B as a reference. This sample had a RIN of 8.2 and a yield of 1.7 ng/mm² tissue. A BioAnalyzer RNA profile from total RNA isolated from experimental rat liver paraffin sections prepared according to the current invention is shown in FIG. 13C. The sample prepared according to the current invention had a RIN of 7.1 and a yield of 3.6 ng/mm² tissue.

Example 10

Figure 14:
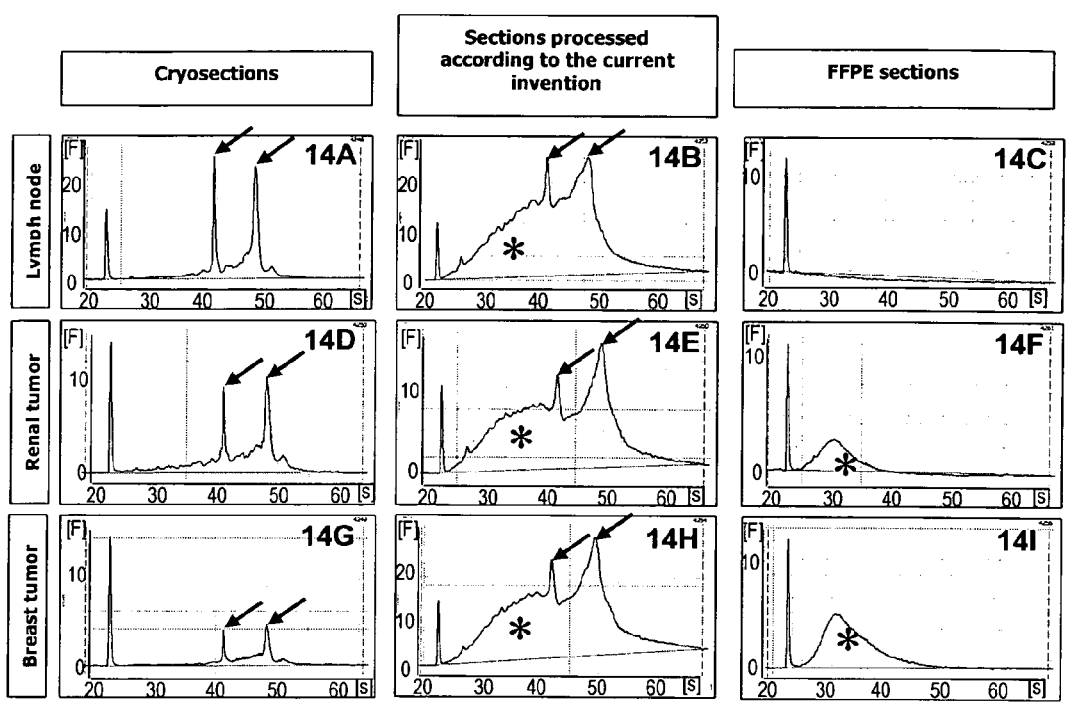
FIG. 14 shows the comparison of the quality of total RNA isolated from cryosections and from FFPE and human "mirror" samples processed according to the current invention.

Comparison of the Quality of Total RNA Isolated from Cryosections Versus Paraffin Section Prepared According to the Current Invention Versus FFPE Human "Mirror" Sections Human lymph node (FIGS. 14A, 14B, 14C), renal tumor (FIGS. 14D, 14E, 14F) and breast tumor (FIGS. 14G, 14H, 14I) tissue were processed in the pathology laboratory. After lamination, a representative segment was cryoprocessed (snap-frozen and embedded in O.C.T. compound) for rapid diagnosis, several representative segments were formalin-fixed and paraffin-embedded according to routine pathology protocols for more detailed diagnosis and a surplus segment was processed according to the procedure as described in the invention. Therefore, we could compare the RNA quality of triplet segments derived from a single specimen (identical agonal state, therapy and post-ischemic interval). Sections were made nuclease-free and all following procedures were performed under nuclease-free conditions. Total RNA was extracted and analyzed according to the procedure described in example 9. The duration of the proteinase K digestion was optimized for both paraffin sections from the current invention and FFPE sections. For RNA extraction from cryosections, the procedure performed was basically the same as for paraffin sections with the omission of the deparaffination and proteinase K digestion steps. The total RNA profiles are depicted in FIG. 14. As can be seen from FIGS. 14A, 14D and 14G, the total RNA isolated from frozen sections was of excellent quality for the 3 tissue types tested (RIN values respectively 9.3; 7.5 and 8.3). These RNA samples represent the "initial RNA quality" of the human tissues, which is of critical importance because the golden rule "garbage in, garbage out" also applies to tissue fixation. The RNA isolated from paraffin sections prepared according to the current invention (FIGS. 14B, 14E and 14H) is of good quality, i.e. the RNA profiles display clear rRNA peaks (arrows), but the RIN values could not be determined due to shifted baselines (N/A). There is some RNA degradation as can be seen from an increase of the RNA species with shorter fragment length (stars). The RNA isolated from FFPE sections (FIGS. 14C, 14F and 14I) is of very poor quality, i.e. the RNA profiles display no rRNA peaks at all, only short fragment RNA species are detected (stars) and the RIN values are low (respectively N/A, 2.2 and 2.2).

Example 11

RT-QPCR on Breast Tumor Tissue Processed According to Standard Procedures (FFPE) or According to the Current Invention A breast cancer biopsy was FFPE and a similar surplus sample was prepared using a method of the present invention. The latter was incubated in FDC solution comprising 10% (v/v) formaldehyde, 65% (v/v) methanol, 5% (v/v) acetic acid and 20% (v/v) diethylether. The surplus sample was subsequently treated with clearing solution comprising diethylether, infiltrated in low-melting paraffin at 52 deg C. and embedded in casting paraffin.

Figures 1, 15:
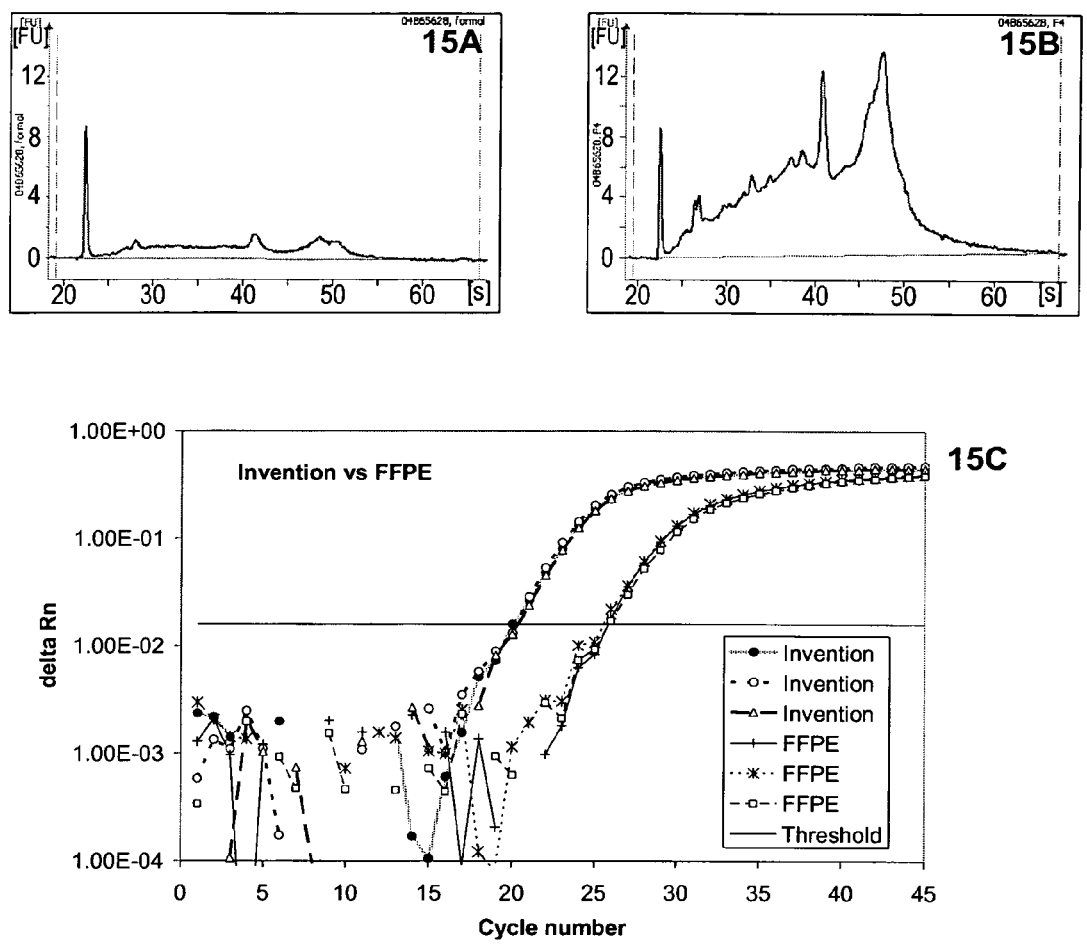
FIG. 15 shows the results from RT-qPCR for Her-2/Neu performed on FFPE breast tumor versus "mirror" surplus samples processed according to the described invention. A comparison between a Her-2 negative and Her-2 positive breast tumor processed according to the current invention is also shown.
Figures 2, 15:
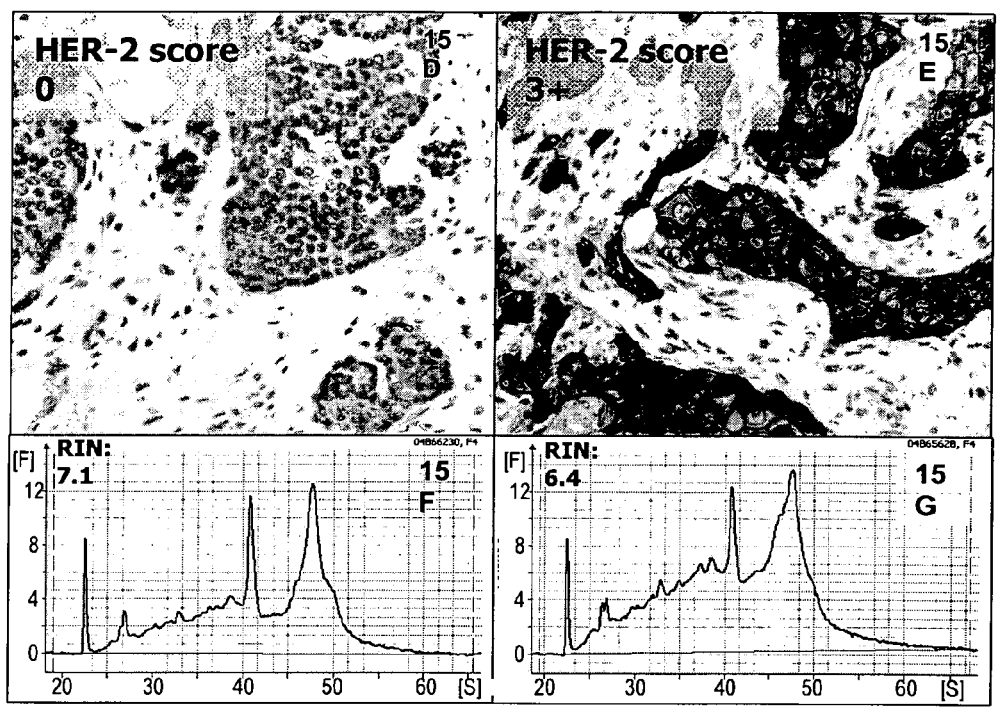
Figure 15:
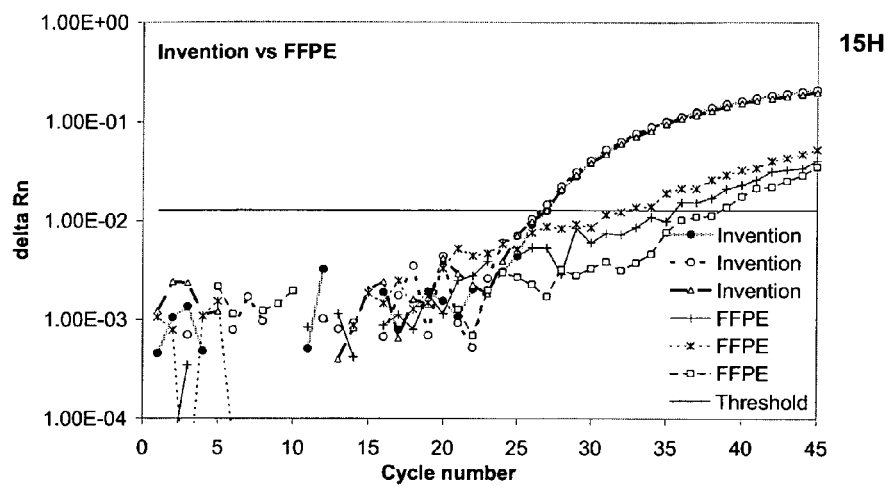
Figure 3:
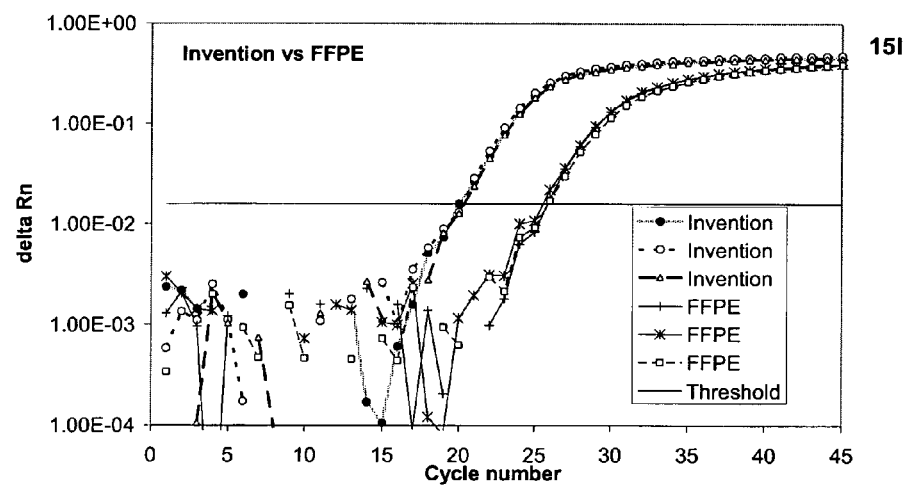

Sections were made nuclease-free and all following procedures were performed under nuclease-free conditions. Total RNA was extracted according to the procedure described in Example 10. RNA quality was evaluated as demonstrated in Examples 9 and 10. The RNA integrity number and RNA concentration were determined for both treated samples using the Agilent RNA profiling technology as described in Example 9. FIG. 15A shows the RNA profile obtained from FFPE sections, FIG. 15A shows the RNA profile obtained from a sample treated using methods of the current invention. Using the classical FFPE method, the RIN was 4.2 and the RNA concentration per mm² tissue was 70 ng/µl. Using the present invention, the RIN was 6.4 and the RNA concentration per mm² tissue was 360 ng/µl. So both RNA yield and quality were poorer in FFPE tissue than in tissue processed according to the current invention.

In a further test, the RNA extract from both samples was tested for the expression of the Her-2/neu gene using reverse transcription and quantitative real-time PCR (RT-qPCR). The results shown in FIG. 15C, roughly indicate a $2^{(25.7-20.2)}$ or 45 times higher concentration of the Her-2/neu transcript in the sample treated according to the present invention compared with FFPE.

In addition, a comparison was made between a two breast cancer biopsies processed according to the current invention—one that is HER-2 negative (FIG. 15D) and another that is HER-2 positive (score 3+, FIG. 15E). RNA was extracted and analyzed according to Examples 9 and 10. As can be seen in FIGS. 15F and 15G, both samples have total RNA of good quality (intact ribosomal peak profile) with respective RIN values of 7.1 and 6.4. Both samples were tested for the expression of the Her-2/neu gene using reverse transcription and quantitative real-time PCR (RT-qPCR). The results shown in FIGS. 15H and 15I, roughly indicate a $2^{(27-20)}$ or 128 times higher concentration of the Her-2/neu transcript in the HER-2 positive sample than in the HER-2 negative sample.

Example 12

Figure 16:
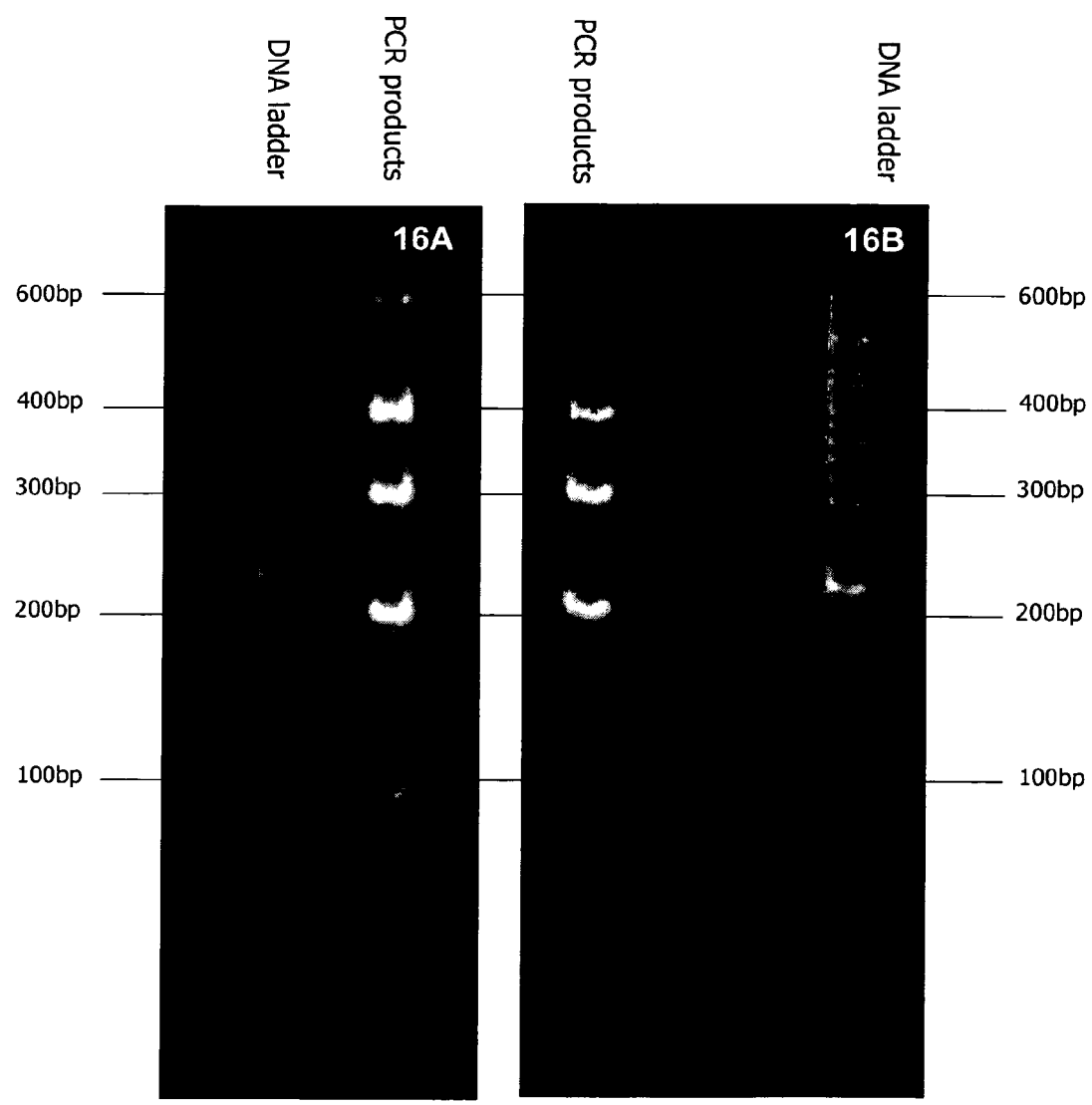
FIG. 16 shows a polyacrylamide gel loaded with amplicons generated with DNA isolated from flash-frozen versus "mirror" surplus tissue samples processed according to the described invention.

Fragment Length of PCR Products Amplified from DNA Isolated from Cryosections Compared to Paraffin Sections Prepared According to the Methods of the Invention DNA was isolated from the nuclease-free cut sections (e.g. with the Dneasy kit from Qiagen, Hilden, Germany). Control multiplex PCR was performed for the evaluation of the quality and amplifiability of DNA extracted from lymphomas. The PCR products were separated electrophoretically. FIG. 16A shows PCR products generated with DNA extracted from a cryosection. Amplicons with a fragment length of 600 bp are clearly visible. FIG. 16B shows PCR products generated with DNA extracted from a paraffin section prepared according to the current invention. Amplicons with a fragment length of 400 bp are clearly visible, small amounts of PCR products with a length of 600 bp are still present.

Example 13

Figure 17:
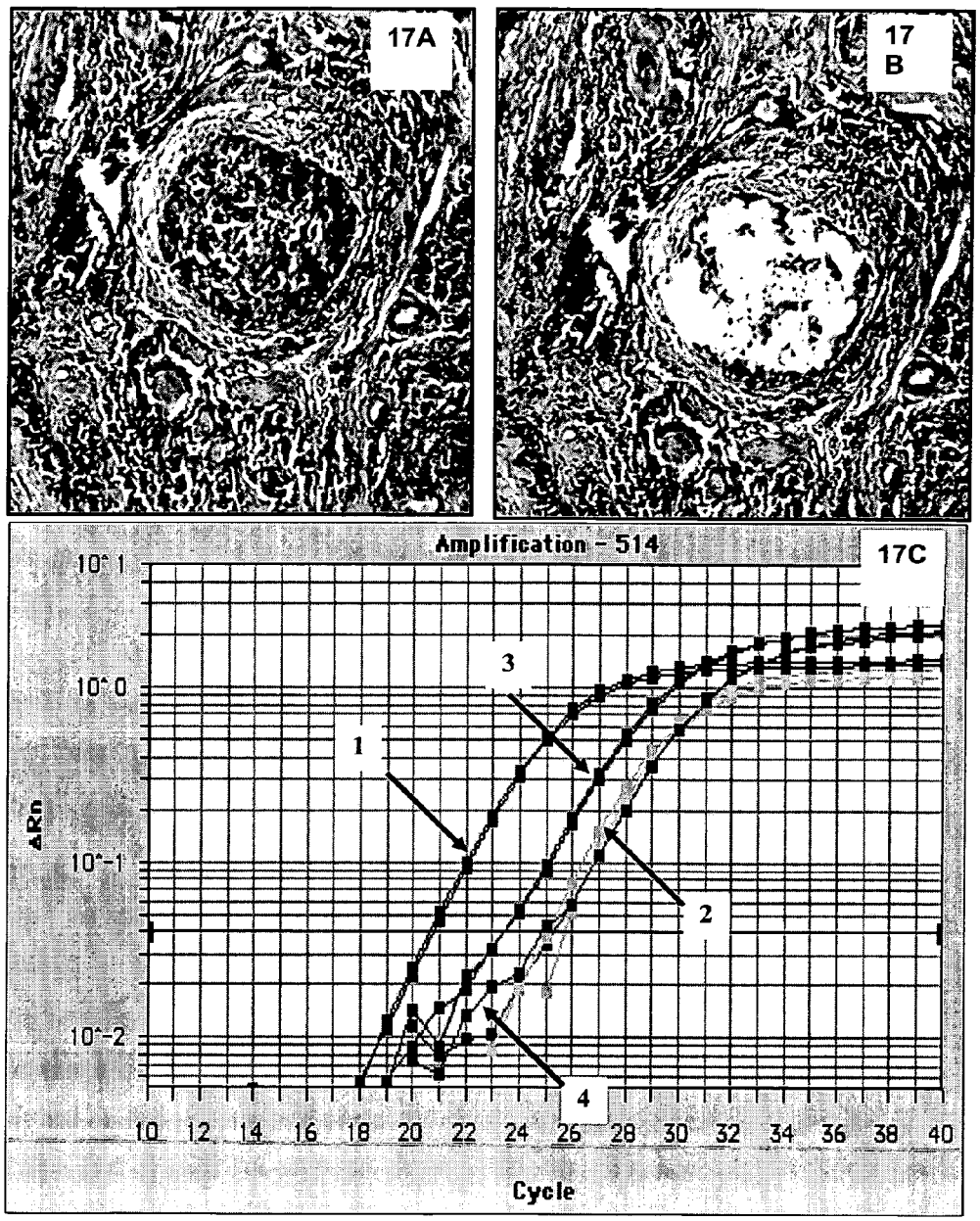
FIG. 17 shows the results from qPCR for the Her/Neu gene performed after laser capture microdissection of tumor cells from breast tumor tissue processed according to the described invention.

Her/Neu DNA Amplification on Breast Tumor Tissue Processed According to Standard Procedures (FFPE) or According to the Current Invention Breast tumor sections prepared according to the current invention and sectioned under nuclease-free conditions were stained with a nuclear histological stain (MethylGreen) and tumor cells were laser capture microdissected (LCM). All procedures were performed under nuclease-free conditions. FIG. 17A shows the section before LCM and FIG. 17B shows the section after LCM isolation of a tumor nest. DNA was isolated from the captured cells (e.g. with the Dneasy kit from Qiagen, Hilden, Germany) and Her-2/Neu DNA amplification was analysed with qPCR (FIG. 17C). Plots 1 and 2 (light plot) are the amplification plots for Her-2 gene and plots 3 and 4 (dark plot) are the amplification plots for the reference gene. Amplification plots 1 and 3 correspond with the IHC Her-2 positive tumor and amplification plots 2 and 4 correspond with the HER-2 negative tumor. While the plots for the reference gene are practically identical for both breast tumor samples, the amplification plot of the Her-2+tumor has clearly shifted to the left, which clearly indicates that a larger number of copies of the Her-2 gene are present in the Her-2+ tumor prepared according to the current invention.

Example 14

RNA Quality from Sections Stained Histologically (Nuclear Stainings) for Laser Microdissection (LCM): Comparison of the Quality of RNA Derived from Cryosections Versus Paraffin Sections Prepared According to the Current Invention Before LCM The recognition of cellular heterogeneity is fundamental for any effective gene expression strategy for solid tissue specimens. Failure to take this diversity into account invariably leads to averaging of the genetic information contained within different cell types within a tissue. A technique that represents the ultimate harmonization between the two disciplines of histopathology and molecular biology is laser microdissection (LCM). LCM allows for the selective collection of cells of interest from heterogeneous tissue sections. To identify the specific cells for LCM, conventional histological stains, as well as immunohistochemical or immunofluorescent labelling have been used. LCM is performed on histological sections that are not cover-slipped. This results in reduced cellular detail, which diminishes the ability to distinguish different cell populations. Ideally, histochemical stains should provide acceptable morphology in order to enable LCM of the correct cell type. In addition, the stain should not interfere with the macromolecules of interest or the subsequent techniques used for molecular analysis. Some cell types (e.g. tumor cells) can be distinguished from surrounding heterogenous cell populations after a simple histological nuclear staining on the basis of their nuclear morphology. If nuclear acid analyses are to be performed after laser capture microdissectie (LCM) of the relevant cell population, it is of critical importance that the stainings are performed quickly and nuclease-free, to prevent RNA depletion and degradation.

Figure 18:
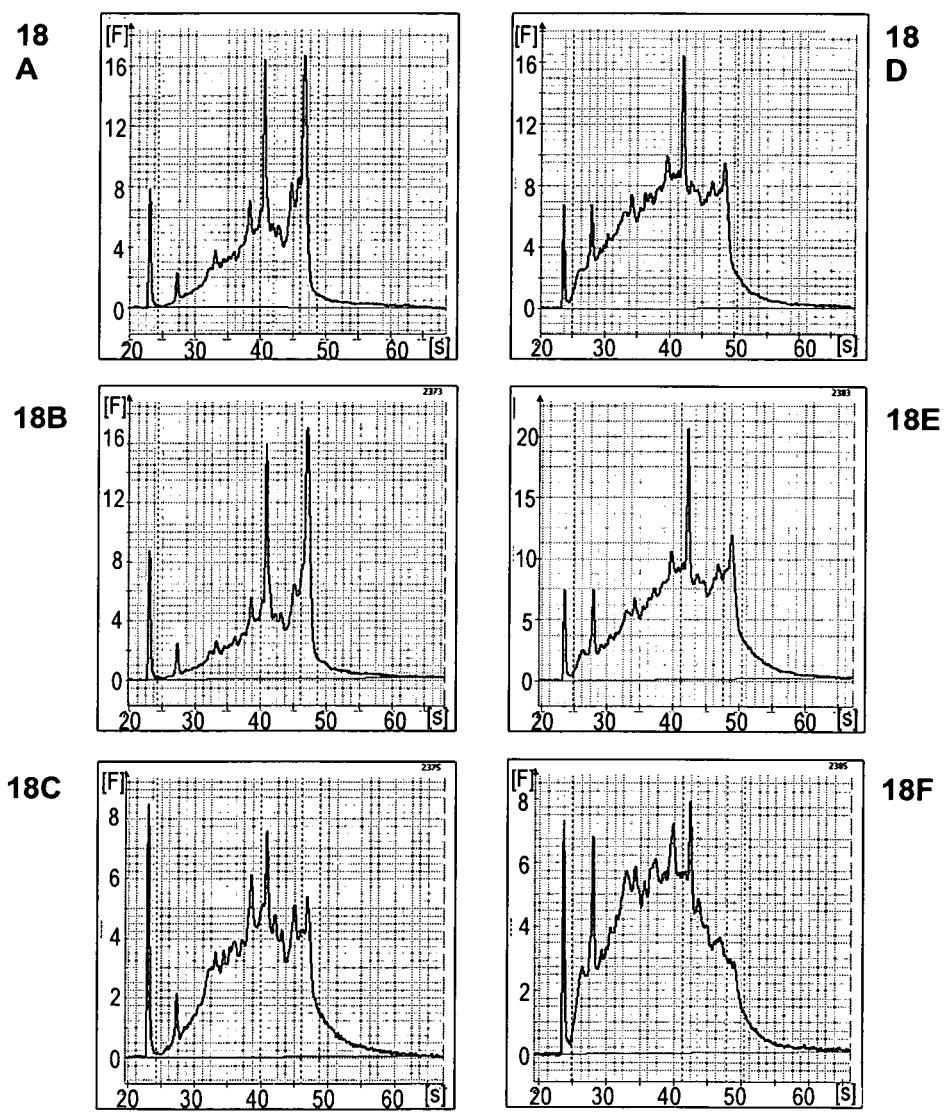
FIG. 18 shows the comparison of the quality of total RNA isolated from histological stained rat liver sections for LCM (different nuclear stainings). The RNA extracted from complete cryosections and from paraffin sections prepared according to the current invention were compared.

Short nuclease-free nuclear stainings were optimized for LCM with the Arcturus PixCell II system. Twin samples of rat liver were flash-frozen end embedded in O.C.T.-compound or processed according to the current invention. All sections were made nuclease-free and all procedures were performed under nuclease-free conditions. Cryosections were fixed shortly in paraformaldehyde at 4 deg C. After this a short nuclear staining was performed with Methylgreen (FIGS. 18B and 18E; Vector Laboratories) or Hematoxylin QS (FIGS. 18C and 18F; Vector Laboratories) or the sections were kept in an aqueous milieu during the staining procedure (FIGS. 18A and 18D; unstained sections). This was followed by the dehydration procedure for LCM as proposed by Arcturus. Paraffin sections prepared according to the current invention were deparaffinized and subsequently stained and dehydrated in an identical way as the cryosections. RNA extraction procedures were performed as described in Example 9. Total RNA profiles and RIN data (Table 2) demonstrated that the Methylgreen staining was better for RNA retention and preservation of RNA quality than the hematoxylin staining as is described in literature (Okuducu A-F, Janzen V, Hahne J C, Ko Y, Wernert N: Influence of histochemical stains on quantitative gene expression after laser-assisted microdissection. Int J Mol Med 11: 449-453, 2003) and this for both cryomaterial as for tissue prepared according to the method of the invention. Indeed, the sections stained with Hematoxylin QS show a decrease of the rRNA peak height (cryosections) or a disappearance of the 28S rRNA peak (paraffin section prepared according to the current inventions while the total RNA profiles of unstained and Methylgreen stained sections were comparable. This was reflected in the RIN data, that were decreased in Hematoxylin QS stained sections and that were comparable in unstained and Methylgreen stained sections (Table 2).

TABLE 2

RIN data

|  | Cryosections | Sections prepared according to the current invention |
|---|---|---|
| Unstained section | 5.4 | 3.3 |
| Methylgreen stained section | 6.7 | 3.7 |
| Hematoxylin QS stained section | 3.3 | 2.7 |

Example 15

Figure 19:
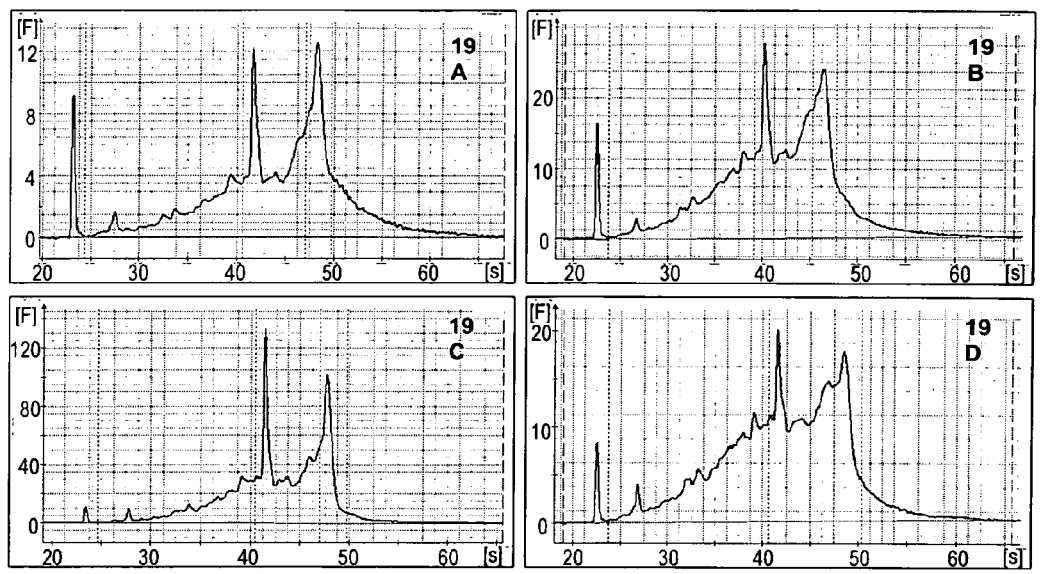
FIG. 19 shows the effect of storage of paraffin blocks prepared according to the current invention on total RNA quality. Stability of total RNA in stored FFPE blocks was compared to RNA stability in paraffin blocks prepared according to the current invention.

Stability of RNA in stored paraffin blocks, prepared according to the described invention. A systematic evaluation of the RNA stability in paraffin tissue blocks prepared according to the methods of the current invention was performed (FIG. 19). The paraffin blocks were sectioned RNase-free with disposable knives and all following procedures were performed nuclease-free. From each block two 10 μm sections were made. The sections were deparaffinized, digested with proteinase K for 3 hours followed by a precipitation step and extracted and analysed as described in Example 9. The total RNA profiles depicted in FIGS. 19A and 19B were derived from RNA extracted from the same tissue block, extracted at time 0 and after 4 months of storage at room temperature respectively. The total RNA profiles depicted in FIGS. 19C and 19D were derived from RNA extracted from the same tissue block, extracted at time 0 and after 6 months of storage at room temperature respectively. After storage, the RNA quality is still good (clearly visible rRNA peaks are still present in FIGS. 19B and 19D). Storage at room temperature induced limited degradation of the RNA inside the paraffin blocks prepared according to the current invention as can be concluded from the slightly decreased RIN numbers (respectively for FIGS. 19A, 19B, 19C and 19D are 7.4; 6.9; 6.4 and 3.7).

Example 16

Figure 20:
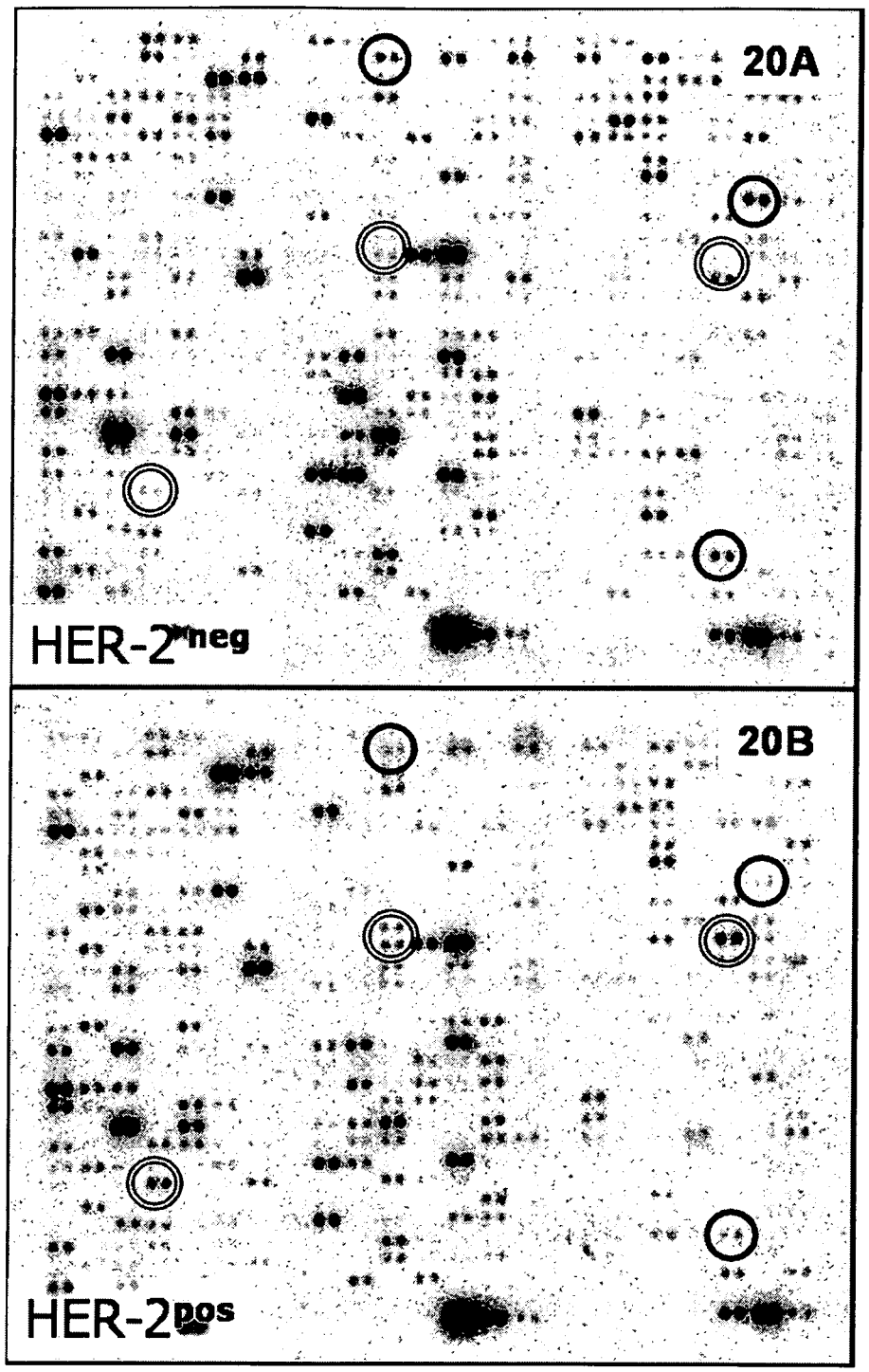
FIG. 20 shows the hybridized and developed nylon membranes of a macroarray analysis performed on RNA extracted from breast tumour tissue processed according to the current invention.

Macroarray Analysis of Breast Tumor Tissues Processed According to the Method of the Current Invention RNA was extracted from laser microdissected cells, isolated from breast tumors processed according to the current invention and analyzed on a nylon membrane macroarray. With this technique, the expression profile of approximately 600 genes, involved in apoptosis and cell cycle, could be studied. The results are shown in FIG. 20. The top membrane (FIG. 20A) shows the array of an HER-2 negative tumor and the bottom membrane (FIG. 20B) shows the array of an HER-2 positive tumor. Genes that were down-regulated (single bold circles) in the HER-2 positive sample were: G1/S-specific cyclin D1, cyclin PRAD1 and Bcl-1 oncogen. Examples of genes that were up-regulated (double circles) in the HER-2 positive sample were: ubiquitin, ezrin (cytovillin, villin 2), C-erbB2 receptor protein tyrosin kinase (HER-2).

What is claimed is:

1. A vial package for a sample processing station comprising:
   a vial configured to receive and retain liquids therein, comprising a vial body and a resealable lid configured to fittingly and reversibly seal a top opening of the vial, and a tissue sample cassette,
wherein the vial body, resealable lid or the tissue sample cassette is provided with a data logging device configured to electronically register and store data regarding a sample and conditions wherein said sample is processed, wherein said data logging device comprises:
   a memory storage component configured to store said data, such that said data remains in association with the vial body, resealable lid or tissue sample cassette;
   means for monitoring time (t) of a non-preset period during which said sample is processed, which time data is stored in said memory storage component; and
   an on/off function adapted to activate/deactivate the data logging device, such that said monitoring takes place once the data logging device has been activated, the tissue sample cassette is connected to the resealable lid by means of an elongated member
wherein the vial package is autonomous, and is configured for removable insertion into the tissue processing station.

2. The vial package according to claim 1, wherein the elongated member is configured to position the tissue sample cassette within the lower half of the inner space of the vial body when the lid seals the top opening of the vial.

3. The vial package according to claim 1, wherein said data logging device is provided on the vial body or on the resealable lid.

4. The vial package according to claim 1, wherein said data logging device is provided on the elongated member.

5. The vial package according to claim 1, wherein said data logging device is provided on the tissue sample cassette, preferably in a cavity of said tissue sample cassette, more preferably embedded in a suitable matrix in the cavity of said tissue sample cassette.

6. The vial package according to claim 1, wherein said data logging device comprises means for monitoring time (t) during which said sample is processed and means for monitoring temperature (T) of the sample in function of time (t).

7. The vial package according to claim 1, wherein said on/off function is adapted to be activated manually or automatically.

8. The vial package according to claim 1, wherein said data logging device comprises a clock and/or timer.

9. The vial package according to claim 1, wherein said data logging device comprises a thermometer.

10. The vial package according to claim 1, wherein said data logging device further comprises a sensor capable of measuring electrical conductance.

11. The vial package according to claim 1, wherein said data logging device comprises an identification means capable of identifying said sample.

12. The vial package according to claim 1, wherein said data logging device comprises a memory storage component capable of storing said registered data.

13. The vial package according to claim 1, wherein said data logging device is connectable to a reading device which is adapted to receive, read and process the data registered by said data logging device.

14. The vial package according to claim 1, wherein the vial comprises at least one breakable seal towards the top of the vial, suitable for receiving or removing fluid there through.

15. The vial package according to claim 1, wherein the vial comprises at least one breakable seal towards the top of the vial, suitable for applying positive or negative air pressure to the vial there through.

16. The vial package according to claim 1, wherein the vial comprises at least one breakable seal towards the base of the vial, suitable for receiving fluid there through.

17. A method for processing a tissue sample with the system of claim 1 which comprises activating said data logging device substantially concurrently with:
   (i) the deposition of the tissue sample to be processed into the tissue sample cassette of said system, or
   (ii) the exposure of the tissue sample cassette comprising said tissue sample to a first treatment solution comprising a fixative, in the vial of said system.

18. The method according to claim 17, comprising:
   (i) querying the data logging device to determine the elapsed time during which the tissue sample has been exposed to fixative,
   (ii) comparing said elapsed time with a pre-decided cut-off value,
   (iii) if the elapsed time is greater than said cut-off value, subjecting the tissue sample to post-fixation tissue processing steps, or, if the elapsed time is lower than said cut-off value, calculating the time needed to completely fix the tissue and continuing fixation for said time before subjecting the tissue sample to post-fixation tissue processing steps.

19. The method according to claim 17, comprising:
(i) querying the data logging device to determine the integral sum of temperature as a function of time during which the tissue sample has been exposed to fixative,
(ii) comparing said integral sum with a pre-decided cut-off value,
(iii) if the integral sum is greater than said cut-off value, subjecting the tissue sample to post-fixation tissue processing steps, or, if the integral sum is lower than said cut-off value, calculating the time needed to completely fix the tissue and continuing fixation for said time before subjecting the tissue sample to post-fixation tissue processing steps.

20. The vial package according to claim 1, wherein the elongated member is configured to position the tissue sample cassette within the inner space of the vial, such as to immerse the tissue sample cassette in liquids to be introduced to the vial.

21. The vial package according to claim 1, wherein the physical connection between the elongated member and the tissue cassette is configured to be broken, thereby allowing processing of the sample apart from the lid.

22. The vial package according to claim 1, wherein said data logging device further comprises a means for monitoring temperature (T) of the sample in function of time (t) which temperature data is stored in said memory storage component.

* * * * *

UNITED STATES PATENT AND TRADEMARK OFFICE
CERTIFICATE OF CORRECTION

PATENT NO. : 8,691,165 B2
APPLICATION NO. : 11/997285
DATED : April 8, 2014
INVENTOR(S) : Carla Duymelinck et al.

It is certified that error appears in the above-identified patent and that said Letters Patent is hereby corrected as shown below:

Title page (item 73, Assignee) at line 1, Change "(BM)" to --(BE)--.

Specification

In column 1 at lines 47-48, Change "transcriptosome" to --transcriptome--.

In column 2 at line 53, Change "formaline," to --formalin,--.

In column 11 at line 36, Change "methano-induced" to --methanol-induced--.

In column 14 at lines 59-60, Change "microdisseded" to --microdissected--.

In column 23 at line 34, Change "clock" to --clock,--.

In column 24 at line 33, Change "component" to --component,--.

In column 24 at line 47, Change "component" to --component,--.

In column 27 at line 8, Change "issue" to --tissue--.

In column 32 at line 20, Change "Kieman" to --Kiernan--.

In column 34 at line 29, Change "Glycophrin C" to --Glycophorin C--.

In column 40 at lines 14-15, Change "heterogenous" to --heterogeneous--.

In column 40 at line 47, Change "inventions" to --invention),--.

Claims

In columns 41-43 at lines 45-25, Change the "claims 1-28" to --1. A vial package comprising:

a vial configured to receive and retain liquids therein, comprising a vial body and a resealable lid configured to fittingly and reversibly seal a top opening of the vial, and a tissue sample cassette, wherein the vial or the tissue sample cassette is provided with a data logging device configured to electronically register and store data regarding a sample and conditions wherein said sample is processed, wherein said data logging device comprises:

a memory storage component configured to store said data;

Signed and Sealed this
Eighth Day of December, 2015

Michelle K. Lee
*Director of the United States Patent and Trademark Office* means for monitoring time (t) of a non-preset period during which said sample is processed, which time data is stored in said memory storage component; and an on/off function adapted to activate/deactivate the data logging device, such that said monitoring takes place once the data logging device has been activated, the tissue sample cassette is connected to the resealable lid by means of an elongated member.

2. The vial package according to claim 1, wherein the elongated member is configured to position the tissue sample cassette within the lower half of the inner space of the vial body when the lid seals the top opening of the vial.

3. The vial package according to claim 1, wherein said data logging device is provided on the vial body or on the resealable lid.

4. The vial package according to claim 1, wherein said data logging device is provided on the elongated member.

5. The vial package according to claim 1, wherein said data logging device is provided on the tissue sample cassette, preferably in a cavity of said tissue sample cassette, more preferably embedded in a suitable matrix in the cavity of said tissue sample cassette.

6. The vial package according to claim 1, wherein said data logging device comprises means for monitoring time (t) during which said sample is processed and means for monitoring temperature (T) of the sample in function of time (t).

7. The vial package according to claim 1, wherein said on/off function is adapted to be activated manually or automatically.

8. The vial package according to claim 1, wherein said data logging device comprises a clock and/or timer.

9. The vial package according to claim 1, wherein said data logging device comprises a thermometer.

10. The vial package according to claim 1, wherein said data logging device further comprises a sensor capable of measuring electrical conductance.

11. The vial package according to claim 1, wherein said data logging device comprises an identification means capable of identifying said sample.

12. The vial package according to claim 1, wherein said data logging device comprises a memory storage component capable of storing said registered data.

13. The vial package according to claim 1, wherein said data logging device is connectable to a reading device which is adapted to receive, read and process the data registered by said data logging device.

14. The vial package according to claim 1, wherein the vial comprises at least one breakable seal towards the top of the vial, suitable for receiving or removing fluid there through.

15. The vial package according to claim 1, wherein the vial comprises at least one breakable seal towards the top of the vial, suitable for applying positive or negative air pressure to the vial there through.

16. The vial package according to claim 1, wherein the vial comprises at least one breakable seal towards the base of the vial, suitable for receiving fluid there through.

17. A method for processing a tissue sample with the system of claim 1 which comprises activating said data logging device substantially concurrently with:

(i) the deposition of the tissue sample to be processed into the tissue sample cassette of said system, or (ii) the exposure of the tissue sample cassette comprising said tissue sample to a first treatment solution comprising a fixative, in the vial of said system.

18. The method according to claim 17, comprising:

(i) querying the data logging device to determine the elapsed time during which the tissue sample has been exposed to fixative, (ii) comparing said elapsed time with a pre-decided cut-off value, (iii) if the elapsed time is greater than said cut-off value, subjecting the tissue sample to post-fixation tissue processing steps, or, if the elapsed time is lower than said cut-off value, calculating the time needed to completely fix the tissue and continuing fixation for said time before subjecting the tissue sample to post-fixation tissue processing steps.

19. The method according to claim 17, comprising:

(i) querying the data logging device to determine the integral sum of temperature as a function of time during which the tissue sample has been exposed to fixative, (ii) comparing said integral sum with a pre-decided cut-off value, (iii) if the integral sum is greater than said cut-off value, subjecting the tissue sample to post-fixation tissue processing steps, or, if the integral sum is lower than said cut-off value, calculating the time needed to completely fix the tissue and continuing fixation for said time before subjecting the tissue sample to post-fixation tissue processing steps.

20. (Cancelled)

21. (Cancelled)

22. (Cancelled)

23. (Cancelled)

24. (Cancelled)

25. The vial package according to claim 1, wherein the elongated member is configured to position the tissue sample cassette within the inner space of the vial, such as to immerse the tissue sample cassette in liquids to be introduced to the vial.

26. The vial package according to claim 1, wherein the physical connection between the elongated member and the tissue cassette is configured to be broken, thereby allowing processing of the sample apart from the lid.

27. The vial package according to claim 1, wherein said data logging device further comprises a means for monitoring temperature (T) of the sample in function of time (t) which temperature data is stored in said memory storage component.

28. (Cancelled)--.